(12) United States Patent
Mooney et al.

(10) Patent No.: US 10,647,959 B2
(45) Date of Patent: *May 12, 2020

(54) CELL-FRIENDLY INVERSE OPAL HYDROGELS FOR CELL ENCAPSULATION, DRUG AND PROTEIN DELIVERY, AND FUNCTIONAL NANOPARTICLE ENCAPSULATION

(75) Inventors: David J. Mooney, Sudbury, MA (US); Jaeyun Kim, Gyeonggi-do (KR); Sidi A. Bencherif, Dorchester, MA (US); Weiwei Aileen Li, Norcross, GA (US)

(73) Assignee: President and Fellows of Harvard College, Cambridge, MA (US)

(*) Notice: Subject to any disclaimer, the term of this patent is extended or adjusted under 35 U.S.C. 154(b) by 78 days.

This patent is subject to a terminal disclaimer.

(21) Appl. No.: 14/112,098

(22) PCT Filed: Apr. 12, 2012

(86) PCT No.: PCT/US2012/033208
§ 371 (c)(1),
(2), (4) Date: Jan. 30, 2014

(87) PCT Pub. No.: WO2012/148684
PCT Pub. Date: Nov. 1, 2012

(65) Prior Publication Data
US 2014/0178964 A1    Jun. 26, 2014

Related U.S. Application Data
(60) Provisional application No. 61/479,774, filed on Apr. 27, 2011.

(51) Int. Cl.
| | | |
|---|---|---|
| C12N 5/00 | (2006.01) | |
| A61L 27/52 | (2006.01) | |
| A61L 27/54 | (2006.01) | |
| B82Y 5/00 | (2011.01) | |
| A61L 27/38 | (2006.01) | |
| A61L 27/56 | (2006.01) | |

(52) U.S. Cl.
CPC ............ C12N 5/0012 (2013.01); A61L 27/38 (2013.01); A61L 27/3834 (2013.01); A61L 27/52 (2013.01); A61L 27/54 (2013.01); A61L 27/56 (2013.01); B82Y 5/00 (2013.01); A61L 2300/624 (2013.01); A61L 2400/08 (2013.01); C12N 2533/74 (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 7,072,628 B2 * | 7/2006 | Agashe ............... H04B 7/0874 375/267 |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,427,602 B1 | 9/2008 | Shea et al. |
| 7,575,759 B2 | 8/2009 | Murphy et al. |
| 7,790,699 B2 | 9/2010 | Melvik et al. |
| 8,067,237 B2 | 11/2011 | Mooney et al. |
| 8,273,373 B2 | 9/2012 | Alsberg et al. |

(Continued)

FOREIGN PATENT DOCUMENTS

| | | |
|---|---|---|
| CN | 101655611 A | 2/2010 |
| EP | 0562862 A1 | 9/1993 |

(Continued)

OTHER PUBLICATIONS

Stachowiak et al. 2008. Inverse opal hydrogel-collagen composite scaffolds as a supportive microenvironment for immune cell migration. Journal of Biomedical Materials Research, vol. 85A, pp. 815-828.*
Drury et al. 2003. Hydrogels for tissue engineering: scaffold design variables and applications. Biomaterials, vol. 24, pp. 4337-4351.*
Chung et al. 2007. Surface engineered and drug releasing prefabricated scaffolds for tissue engineering. Advanced Drug Delivery Reviews, vol. 59, pp. 249-262.*
Wall Mar. 2, 2011. Gold nanoparticles used in wound-healing tissue scaffolding. Design and Evaluation of a Composite Tissue Scaffold for Wound Healing. MU Division of Food Systems and Bioengineering seminar Series, 4 Pages.*
Chan et al. 2008. Scaffolding in tissue engineering: general approaches and tissue-specific considerations. European Spine Journal, vol. 17 Supplement 4: S467-S479.*

(Continued)

*Primary Examiner* — Robert J Yamasaki
(74) *Attorney, Agent, or Firm* — McCarter & English, LLP; Maria Laccotripe Zacharakis; Wei Song

(57) ABSTRACT

The invention provides polymer scaffolds for cell-based tissue engineering.

24 Claims, 8 Drawing Sheets

(56) References Cited

U.S. PATENT DOCUMENTS

| | | |
|---|---|---|
| 8,728,456 B2 | 5/2014 | Sands et al. |
| 8,818,058 B2 | 8/2014 | Paul et al. |
| 8,932,583 B2 | 1/2015 | Mooney et al. |
| 2002/0131853 A1 | 9/2002 | Nagasawa |
| 2002/0150604 A1 | 10/2002 | Yi et al. |
| 2003/0075822 A1 | 4/2003 | Slivka et al. |
| 2003/0082606 A1 | 5/2003 | Berenson et al. |
| 2003/0095994 A1 | 5/2003 | Geistlich et al. |
| 2003/0100527 A1 | 5/2003 | Krieg et al. |
| 2003/0232895 A1 | 12/2003 | Omidian et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0220111 A1 | 11/2004 | Kleinman et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0138416 A1 | 6/2008 | Rauh et al. |
| 2008/0206306 A1 | 6/2008 | Jabbari et al. |
| 2008/0268052 A1 | 10/2008 | Voytik-Harbin et al. |
| 2009/0017096 A1 | 1/2009 | Lowman et al. |
| 2009/0123509 A1* | 5/2009 | Berkland ............... A61L 26/008 424/422 |
| 2009/0192079 A1 | 7/2009 | Santos et al. |
| 2009/0238853 A1 | 9/2009 | Liu et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0020216 A1 | 1/2011 | Mooney et al. |
| 2011/0117170 A1 | 5/2011 | Cao et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264699 A1 | 10/2012 | Komatsu et al. |
| 2012/0329791 A1 | 12/2012 | Ashwell et al. |
| 2013/0029030 A1 | 1/2013 | Larsen |
| 2013/0177636 A1 | 7/2013 | Mooney et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0079752 A1 | 3/2014 | Huebsch et al. |
| 2014/0112990 A1 | 4/2014 | Bencherif et al. |
| 2014/0193488 A1 | 7/2014 | Kim et al. |
| 2014/0234423 A1 | 8/2014 | Sands et al. |
| 2015/0024026 A1 | 1/2015 | Mooney et al. |
| 2015/0072009 A1 | 3/2015 | Kim et al. |

FOREIGN PATENT DOCUMENTS

| | | | |
|---|---|---|---|
| EP | 1452191 A2 | 9/2004 | |
| EP | 1561481 A2 | 8/2005 | |
| JP | 2005170816 A | 6/2005 | |
| WO | WO-9616086 A1 | 5/1996 | |
| WO | WO-9801228 A1 | 3/1998 | |
| WO | WO-9951259 A2 | 10/1999 | |
| WO | WO-0135932 A2 | 5/2001 | |
| WO | WO-0216557 A2 | 2/2002 | |
| WO | WO-03020884 A2 | 3/2003 | |
| WO | WO-04006990 A2 | 1/2004 | |
| WO | WO-04030706 A2 | 4/2004 | |
| WO | WO-04089413 A1 | 10/2004 | |
| WO | WO-05026318 A2 | 3/2005 | |
| WO | WO-05037190 A2 | 4/2005 | |
| WO | WO-05037293 A1 | 4/2005 | |
| WO | WO-05046748 A1 | 5/2005 | |
| WO | WO-05072088 A2 | 8/2005 | |
| WO | WO-06119619 | 11/2006 | |
| WO | WO-06136905 A2 | 12/2006 | |
| WO | WO-07030901 A1 | 3/2007 | |
| WO | WO-07064152 A1 | 6/2007 | |
| WO | WO-07070660 A2 | 6/2007 | |
| WO | WO-07078196 | 7/2007 | |
| WO | WO-07107739 A1 | 9/2007 | |
| WO | WO-07150020 A1 | 12/2007 | |
| WO | WO-08018707 A1 | 2/2008 | |
| WO | WO-09002401 A2 | 12/2008 | |
| WO | WO-09005769 A2 | 1/2009 | |
| WO | WO-09074341 A1 | 6/2009 | |
| WO | WO-09102465 A2 | 8/2009 | |
| WO | WO-09146456 A1 | 12/2009 | |
| WO | WO-09155583 A1 | 12/2009 | |
| WO | WO-10120749 A2 | 10/2010 | |
| WO | WO-11014871 A1 | 2/2011 | |
| WO | WO-11063336 A2 | 5/2011 | |
| WO | WO-11109834 A2 | 9/2011 | |
| WO | WO-11130753 A2 | 10/2011 | |
| WO | WO-11150240 A1 | 12/2011 | |
| WO | WO-11151431 A1 | 12/2011 | |
| WO | WO-11163669 A2 | 12/2011 | |
| WO | WO-12009611 A2 | 1/2012 | |
| WO | WO-12019049 A1 | 2/2012 | |
| WO | WO-1204865 A2 | 4/2012 | |
| WO | WO-2012048165 A2 * | 4/2012 | ............ A61L 27/52 |
| WO | WO-12064697 A2 | 5/2012 | |
| WO | WO-1214358 A1 | 11/2012 | |
| WO | WO-12167230 A1 | 12/2012 | |
| WO | WO-13106852 A1 | 7/2013 | |
| WO | WO-13158673 A1 | 10/2013 | |

OTHER PUBLICATIONS

Chevalier et al. 2008. Fabrication of Porous Substrates: A Review of Processes Using Pore Forming Agents in the Biomaterial Field. Journal of Pharmaceutical Sciences, vol. 97, pp. 1135-1154.*

F Hu et al. 2008.Preparation and properties of an injectable scaffold of poly(lactic-co-glycolic acid) microparticles/chitosan hydrogel. JOURNAL OF THE MECHANICAL BEHAVIOR OF BIOMEDICAL MATERIALS, vol. 1, pp. 352-359.*

Gong et al. 2008. Poly (lactic acid) scaffold fabricated by gelatin particle leaching has good biocompatibility for chondrogenesis. Journal of Biomaterials Science Polymer Edition, vol. 19, pp. 207-221.*

XH Wang et al 2003. Covalent immobilization of chitosan and heparin on PLGA surface. International Journal of Biological Macromolecules 33 (2003) 95-100.*

Stachowiak et al., published online Oct. 15, 2007. Inverse opal hydrogel-collagen composite scaffolds as a supportive microenvironment for immune cell migration. Journal of Biomedical Materials Research, vol. 85A, pp. 815-828. (Year: 2007).*

Nicodemus et al. 2008. Cell Encapsulation in Biodegradable Hydrogels for Tissue Engineering Applications. Tissue Engineering Part B vol. 14, No. 2, pp. 149-165. (Year: 2008).*

Ma et al. 2001. Biodegradable Polymer Scaffolds with Well-Defined Interconnected Spherical Pore Network. Tissue Engineering, vol. 7,

(56) References Cited

OTHER PUBLICATIONS

Nu Biodegradable Polymer Scaffolds with Well-Defined Interconnected Spherical Pore Network. Tissue Engineering, vol. 7, No. 1, pp. 23-33. (Year: 2001).*
Guo, Xuan, et al. "Repair of osteochondral defects with biodegradable hydrogel composites encapsulating marrow mesenchymal stem cells in a rabbit model." Acta biomaterialia 6.1 (2010): 39-47. (Year: 2010).*
Shin, Heungsoo, Seongbong Jo, and Antonios G. Mikos. "Modulation of marrow stromal osteoblast adhesion on biomimetic oligo [poly (ethylene glycol) fumarate] hydrogels modified with Arg-Gly-Asp peptides and a poly (ethylene glycol) spacer." Journal of Biomedical Materials Research 61.2 (2002): 169-179. (Year: 2002).*
Yang, Fan et al., "The effect of incorporation RGD adhesive peptide in polyethlene glycol diacrylate hyrdogel on osteogenesis of bone marrow stromal cells," *Biomaterials*, vol. 25(2005):5991-5998.
"Collagen: The Fibrous Proteins of the Matrix," *Molecular Cell Biology*. Lodish et al., eds. New York: W.H. Freeman. Section 22.3(2000):979-985.
"Transient." Merriam-Webster Dictionary. Web. Jul. 18, 2014. www.merriam-webster.com/dictionary/transient.
Agache et al."Mechanical Properties and Young's Modulus of Human Skin in Vivo." *Arch. Dermatol. Res.* 269.3(1980):221-232.
Aguado et al. "Improving Viability of Stem Cells During Syringe Needle Flow Through the Design of Hydrogel Cell Carriers," *Tissue Eng. Part A*. 18.7-8(2012):806-815.
Akpalo et al. "Fibrin-Polyethylene Oxide Interpenetrating Polymer Networks: New Self-Supported Biomaterials Combinging the Properties of Both Protein Gel and Synthetic Polymer." *Acta Biomater.* 7.6(2011):2418-2427.
American Diabetes Association. "Standards of Medical Care in Diabetes—2013," *Diabetes Care*. 36.S1(2013):S11-S66.
Annaidh et al. "Characterization of the Anistropic Mechanical Properties of Excised Human Skin." *J. Mech. Behav. Biomed. Mater.* 5.1(2012):139-148.
Aschner et al. "Metabolic Memory for Vascular Disease in Diabetes." *Diabetes Technol. Ther.* 14.S1(2012):S68-S74.
Aubin et al. "Directed 3D Cell Alignment and Elongation in Microengineered Hydrogels." *Biomater.* 31.27(2010):6941-6951.
Babensee et al. "Host Response to Tissue Engineered Device." *Adv. Drug Deli. Rev.* 33.1-2(1998):111-139.
Becker et al. "Cytological Demonstration of the Clonal Nature of Spleen Colonies Derived from Transplanted Mouse Marrow Cells." *Nature.* 197(1963):452-454.
Bell, "Models for the Specific Adhesion of Cells to Cells." *Science.* 200 4342(1978):618-627.
Bencheril et al. "Influence of Cross-Linker Chemistry on Release Kinetics of PEG-co-PGA Hydrogels." *J. Biomed. Mater. Res. A.* 90.1(2009):142-153.
Bencherif et al. "End-Group Effects on the Properties of PEG-*co*-PGA Hydrogels." *Acta Biomater.* 5.6(2009):1872-1863.
Bencherif et al. "Influence of the Degree of the Methacrylation of Hyaluronic Acid Hydrogels Properties." *Biomater.* 29.12(2008):1739-1749.
Bencherif et al. "Injectable Preformed Scaffolds with Shape-Memory Properties." *PNAS.* 109.48(2012):19590-19595.
Bencherif et al. "Nanostructured Hybrid Hydrogels Prepared by a Combination of Atom Transfer Radical Polymerization and Free Radical Polymerization." *Biomater.* 30.29(2009):5270-5278.
Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.
Benton et al. "Photocrosslinking of Gelatin Macromers to Synthesize Porous Hydrogels that Promote Valvular Intersitial Cell Function." *Tissue Eng. Part A.* 15.11(2009):3221-3230.
Berg et al. "IL-10 is a Central Regulation of Cyclooxygenase-2 Expression and Prostaglandin Production." *J. Immunol.* 166.4(2001):2674-2680.

Bergstraesser et al. "Stimulation and Inhibition of Human Mammary Epithelial Cell Duct Morphogenesis In Vitro." *Proc. Assoc. Am. Physicians.* 108.2(1996):140-154.
Bianco et al. "The Meaning, the Sense and the Significance: Translating the Science of Mesenchymal Stem Cells into Medicine." *Nat. Med.* 19.1(2013):35-42.
Bilodeau et al. "Regular Pyramid Punch Problem," *J. Appl. Mech.* 59.3(1992):519-523.
Boaleng et al. "Wound Healing Dressings and Drug Delivery Systems: A Review." *J. Pharm. Sci.* 97.8(2008):2892-2923.
Boerckel et al. "Mechanical Regulation of Vascular Growth and Tissue Regeneration in vivo." *PNAS.* 108.37(2011):E674-E680.
Boontheekul et al. "Controlling Alginate Gel Degradation Utilizing Partial Oxidation and Bimodal Molecular Weight Distribution." *Biomaterials.* 26.15(2005):2455-2465.
Brignone et al. "A Phase I Pharmacokinetic and Biological Correlative Study of IMP321, a Novel MHC Class II Agonist, in Patients with Advanced Renal Cell Carcinoma." *Clin. Cancer Res.* 15.19(2009):6225-6231.
Broxmeyer et al. "Insights into the Biology of Cord Blood Stem/Progenitor Cells." *Cell Prolif.* 44.S1(2011):55-59.
Buckwalter et al. "Form of Antigen Dictates Immunity: Irradiated Cell vs. Whole Cell Lystate Vaccination," *J. Immunol.* 178(2007).
Bullard et al. "Fetal Would Healing: Current Biology." *World J. Surg.* 27.1(2003):54-61.
Buonaguro et al. "Translating Tumor Antigens into Cancer Vaccines." *Clin. Vaccine Immunol.* 18.1(2011):23-34.
Burdick et al. "Controlled Degradation and Mechanical Behavior of Photopolymerized Hyaluronic Acid Networks." *Biomacromol.* 6.1(2005):386-391.
Burdick et al. "Photoencapsulation of Osteoblasts in Injectable RGD-Modified PEG Hydrogels for Bone Tissue Engineering." *Biomater.* 23.22(2002):4315-4323.
Bégué et al. "Vaccination Against Human Papillomavirus. Implmentation and Efficacy Against Cervical Cancer Control." *Bull. Acad. Natl. Med.* 191.9(2007):1805-1816. (French original and English abstract).
Bürger et al. "Effect of VEGF and its Receptor Antagonist SU-5416, an Inhibitor of Angiogenesis, on Processing of the $\beta$-amyloid Precursor Protein in Primary Neuronal Cells Derived From Brain Tissue of Tg2576 Mice." *Int. J. Dev. Neurosci.* 28.7(2010):597-604.
Cameron et al. "The Influence of Substrate Creep on Mesenchymal Stem Cell Behaviour and Phenotype." *Biomater.* 32.56(2011):5979-5993.
Caufield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.
Ceriello et al. "The 'Metabolic Memory': Is more than just Tight Glucose Control is Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.5-6(2012):133-138.
Chan et al. "Traction Dynamics of Filopodia on Compliant Substrates." *Science.* 322.5908(2008):1687-1691.
Chang. "Mouse Models for Studies of Retinal Degeneration and Diseases." *Methods Mol. Biol.* 935(2013):27-39.
Chen et al. "Adipogenic Differentiation of Adipose Tissue-Derived Human Mesenchymal Stem Cells: Effects of Gastric Bypass Surgery." *Surg. Endosc.* 26(2012):3449-3456.
Chen et al. "Functional Human Vascular Network Generated in Photocrosslinkable Gelatin Methacrylate Hydrogels." *Adv. Funct. Mater.* 22.10(2012):2027-2039.
Chiang et al. "Whole Tumor Antigen Vaccines." *Semin. Immunol.* 22.3(2010):132-143.
Choi et al. "In Vitro Mineralization by Preosteoblasts in Poly(D-lactide-co-glycolide) Inverse Opal Scaffolds Reinforced with Hydrozyapatile Nanoparticles." *Langmuir.* 26.14(2010):12126-12131.
Choi et al. "Three-Dimensional Scaffolds for Tissue Engineering: The Importance of Uniformity in Pore Size and Structure." *Langmuir.* 26.24(2010):19001-19006.

(56) References Cited

OTHER PUBLICATIONS

Chou et al. "Characterization of Photocross Linked Alginate Hydrogels for Nucleus Puiposus Cell Encapsulation." *J. Biomed. Mater. Res. A.* 91A.1(2009):187-194.
Clark et al. "Myosin II and Mechanotransduction: A Balancing Act." *Trends Cell Biol.* 17.4(2007):178-186.
Cosimar et al. "Engineering RGD Nanopatterned Hydrogels to Control Preosteoblast Behavior: A Combined Computational and Experimental Approach." *Biomaterials.* 26(2007):4409-4417.
Cook et al. "A Sialomucopeptide Liberated by Trypsin from the Human Erythrocyte." *Nature.* 188(1960):1011-1012.
Cooper. "Metabolic Memory: Implications for Diabetic Vascular Complications." *Pediatr. Diabetes.* 10.5(2009):343-346.
Cuda et al. "In Vitro Actin Filament Sliding Velocities Produced by Mixtures of Different Types of Myosin." *Biophys. J.* 72.4(1997):1767-1779.
Cukierman et al. "Taking Cell-Matrix Adhesions to the Third Dimension." *Science.* 294.5547(2001):1708-1712.
David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.
de Jorg et al. "Regulation of Notch Signaling Genes During BMP2-Induced Differentiation of Osteoblast Precursor Cells." *Biophys. Res. Commun.* 320(2004):100-107.
Dembo et al. "Stresses at the Cell-to-Substrate Inferface During Locomotion of Fibroblasts." *Biophys. J.* 76.4(1999):2307-2316.
Dexter et al. "Conditions Controlling the Proliferation of Haemopoietic Stem Cells In Vitro." *J. Cell. Physiol.* 91.3(1977):335-344.
Di Nicola et al. "Human Bone Marrow Stromal Cells Supress T-Lymphocyte Proliferation Induced by Cellular or Nonspecific Mitogens Stimuli." *Blood.* 99.10(2002):3838-3843.
Diduch et al. "Two Cell Lines from Bone Marrow tht Differ in Terms of Collegen Synthesis. Osterogenic Characteristics, and Matrix Mineralization." *J. Bone Joint Surg. Am.* 75.1(1993):92-105.
Diridollou et al. "Skin Ageing: Changes of Physical Properties of Human Skin in vivo." *J. Cosmet. Sci.* 23.6(2001):353-362.
Discher et al. "Tissue Cells Feel and Respond to the Stiffness of their Substrate." *Science.* 310.5751(2005):1139-1143.
Disis et al. "Granulocyte-Macrophage Colony-Stimulating Factor: An Effective Adjuvant for Protein and Peptide-Based Vaccines." *Blood.* 88.1(1996):202-210.
Donati et al. New Hypthesis on the Role of Alternating Sequences in Calcium-Alginate Gels. *Biomacromol.* 6.2(2005):1031-1040.
Douay et al. "Ex vivo Production of Human Red Blood Cells from Hematopoietic Stem Cells: What is the Future in Transfusion?" *Transfus. Med. Rev.* 21.2(2007):91-100.
Dranoff. "GM-CSF-Based Cancer Vaccines." *Immunol. Rev.* 188(2002):147-154.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.
Edwards et al. "Evaluation of Biomechanical Properties of Human Skin." *Clin Dermatol.* 13.4(1995):375-380.
Eming et al. "Inflammation in Wound Repair: Molecular and Cellular Mechanisms." *J. Invest. Dermatol.* 127.3(2007):514-525.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1Pt1(2004):617-628.
Exposito et al. "The Fibrallar Collagen Family." *Int. J. Mol. Sci.* 11.2(2010):407-426.
Falanga. "Wound Healing and its Impairment in the Diabetic Foot." *Lancet.* 366.9498(2005):1736-1743.
Fauquemerque et al. "HLA-A° 0201-Restricted CEA-Derived Peptide CAP1 is not a Suitable Target for T-Cell-Based Immunotherapy." *J. Immunother.* 33.4(2010):402-413.

Fisher et al. "The Study of Protein Mechanics with the Atomic Force Microscope." *Trends Biochem. Sci.* 24.10(1999):379-384.
Friedenstein et al. "Fibroblast Precursors in Normal and irradiated Mouse Hematopoietic Organs." *Exp. Hematol.* 4.5(1976):267-274.
Gargel et al. "Traction Stress in Focal Adhesions Correlates Biphysically with Actin Retrograde Flow Speed." *J. Cell Biol.* 183.6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geeriigs et al. "Linear Behavior of Subcutaneous Adipose Tissue." *Biohol.* 45.6(2008):677-688.
GenBank Accession No. AAA36738.1, Aug. 3, 1993.
GenBank Accession No. AAA60022.1, Jan. 7, 1995.
GenBank Accession No. AAA64239.1, Mar. 23, 1995.
GenBank Accession No. AAB18786.3, Jul. 12, 1999.
GenBank Accession No. AAH94877.1, May 20, 2005.
GenBank Accession No. AEO22039.1, Sep. 17, 2011.
GenBank Accession No. AF34424.1, Apr. 8, 2012.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01955.1, Nov. 14, 2006.
GenBank Accession No. DQ103757.1, Jul. 25, 2005.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000572.2, May 18, 2014.
GenBank Accession No. NM_000638.3, May 14, 2014.
GenBank Accession No. NM_000758.3, May 4, 2014.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001845.4, May 3, 2014.
GenBank Accession No. NM_001901.2, May 18, 2014.
GenBank Accession No. NM_002421.3_May 11, 2014.
GenBank Accession No. NM_002982.3, May 3, 2014.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.6, Mar. 31, 2014.
GenBank Accession No. NM_015719.3, Feb. 26, 2014.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001836.2, May 3, 2014.
GenBank Accession No. NP_001892.1, May 18, 2014.
GenBank Accession No. NP_002973.1, May 3, 2014.
GenBank Accession No. NP_003239.2, Feb. 18, 2014.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_056534.2, Feb. 26, 2014.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Graessley. "Entangled Linear, Branched and Network Polymer Systems—Molecular Theories," *Adv. Poly. Sci.* 47(1982):67-117.
Guillaume et al. "Two Abundant Proteasome Subtypes that Uniquely Process Some Antigens Presented by HLA Class I Molecules." *PNAS.* 107.43(2010):18599-18604.

(56) References Cited

OTHER PUBLICATIONS

Guo et al. "Droplet Microfluids for High-Throughput Biological Assays." *Lab Chip*. 12.22(2012):2146-2155.
Gurkan et al. "The Mechanical Environment of Bone Marrow: A Review." *Ann. Biomed. Eng*. 36.12(2008):1978-1991.
Halim et al. "Biologic and Synthesis Skin Substitutes: An Overview." *Indian J. Plast. Surg*. 43(2010):S23-S28.
Harris. "Classification, Diagnostic Criteria, and Screening for Diabetes." *Diabetes in America*. NIH Publication No. 95-1468, Chapter 2. (1995):15-36.
Holland et al. "Transforming Growth Factor-β1 Release from Oligo(poly(ethylene glycol)Fumarate) Hydrogels in Conditions that Model the Cartilage Wound Healing Environment." *J. Control. Release*. 94(2004):101-114.
Humphries et al. "Integrin Ligands at a Glance." *J. Cell. Sci*. 119.Pt19(2006):3901-3903.
Huston et al. "Protein Engineering of Antibody Binding Sites: Recovery of Specific Activity in an Anti-Gigoxin Single-Chain Fv Analogue Produced in *Escherichia coli*." *PNAS*. 85.16(1988):5879-5883.
Huston et al. "Synthesis and Characterization of Tunable Poly(ethylene Glycol): Gelatin Methacrylate Composite Hydrogels." *Tissue Eng. Part A*. 17.13-14(2011):1713-1723.
Hwang et al. "Fabrication of Three-Dimensional Porous Cell-Laden Hydrogel for Tissue Engineering." *Biofabrication*. 2.3(2010):035003.
Ihnal et al. "Hypothesis: The 'Metabolic Memory', the New Challenge of Diabetes." *Diabet. Med*. 24.6(2007)582-586.
Isern et al. "Self-Renewing Human Bone Marrow Mesenspheres Promote Hematopoietic Stem Cell Expansion." *Cell Rep*. 3.5(2013):1714-1724.
Janmey et al. "From Tissue Mechanics to Transcription Factors." *Differentiation*. 86.3(2013):112-120.
Jiang et al. "Two-Piconewton Slip Bond Between Fibronectin and the Cytoskeleton Depends on Taiin." *Nature*. 424.6946(2003):334-337.
Jokinen et al. "Integrin-Mediated Cell Adhesion to Type I Collagen Fibrils." *J. Biol. Chem*. 279.30(2004):31956-31963.
Jugdutt et al. "Aging and Defective Healing, Adverse Remodeling, and Blunted Post-Conditioning in the Reperfused Wounded Heart." *J. Am. Coll. Cardiol*. 51.14(2008):1399-1403.
Kang et al. "Effect of Porous Structure on the Degradation of Freeze-Dried Gelatin Hydrogels." *J. Bioact. Compat. Poly*. 14.4(1999):331-343.
Katayama et al. "Integrated Analysis of the Genome and the Transcriptome by FANTOM." *Brief Bioinform*. 5.3(2004):249-258.
Kearney et al. "Macroscale Delivery Systems for Molecular and Cellular Payloads." *Nat. Mater*. 12.11(2013):1004-10017.
Kennedy et al. "Rapid and Extensive Collapse from Electrically Responsive Macroporous Hydrogels." *Adv. Healthc. Mater*. 3.4(2014):500-507.
Khetan et al. "Degradation-Mediated Cellular Traction Directs Stem Cell Fate in Covalently Crosslinked Three-Dimensional Hydrogels." *Nat. Mater*. 12.5(2013):458-465.
Kim et al. "Multifunctional Capsule-in-Capsule for Immunoprotection and Trimodal Imaging." *Angew. Chem. Int. Ed*. 50.10(2011):2317-2321.
Klein et al. "Cell-Cycle Control by Physiological Matrix Elasticity and In Vivo Tissue Stiffening." *Curr. Biol*. 19.18(2009):1511-1518.
Kohane. "Microparticles and Nanoparticles for Drug Delivery." *Biotechnol. Bioeng*. 96.2(2007):203-209.
Kong et al. "FRET Measurements of Cell-Traction Forces and Nano-Scale Clustering of Adhesion Ligands Varied by Substrate Stiffness." *PNAS*. 102.12(2005):4300-4305.
Kratky et al. "Direct Activation of Antigen-Presenting Cells in Required for CD8+ T-Cell Priming and Tumor Vaccination." *PNAS*. 108.42(2011):17414-17419.
Kuwahara et al. "Cell Delivery Using an Injectable and Adhesive Transglutaminease-Gelatin Gel." *Tissue Eng. Part C Methods*. 16.4(2010):609-618.

Lee et al. "Intravenous hMSCs Improve Myocardial Infarction in Mice because Cells Embolized in Lung are Activated to Secrete the Anti-Inflammatory Protein TSG-6." *Cell Stem Cell*. 5.1(2009):54-63.
Lee et al. "Engineering Liver Tissue Spheroids with Inverted Colloidal Crystal Scaffolds." *Biomater*. 30.27(2009):4687-4694.
Lele et al. "Investigating Complexity of Protein-Proetin Interactions in Focal Adhesions." *Biochem. Biophys. Res. Commun*. 369. 3(2008):929-934.
Levental et al. "Soft Biological Materials and their Impact on Cell Function." *Soft Matter*. 3(2007):299-306.
Li et al. "A Novel Cyclohexene Derivate, Ethyl ($6R$)-6-[$N$-(2-Chioro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol*. 69.4(2006):1288-1295.
Li et al. "Purified Hybrid Cells from Dendritic Cell and Tumor Cell Fusions are Superior Activators of Antitumor Immunity." *Cancer Immunol. Immunother*. 50.9(2001):456-462.
Lin et al. "Transdermal Regulation of Vascular Network Bioengineering Using a Photopolymerizable Methacrylated Gelatin Hydrogel." *Biomater*. 34.28(2013):6785-6796.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." *Tissue Eng*. 13.5(2007):1133-1124.
Liu et al. "On the Viscoelastic Character of Liver Tissue: Experiments and Modeling of the Linear Behaviour." *Bioheol*. 37.3(2000):191-201.
Lo et al. "Cell Movement is Guided by the Rigidity of the Substrate." *Biophys. J*. 79.1(2000):144-152.
Ludewig et al. "Immunotheraphy with Dendritic Cells Directed Against Tumor Antigens Shared with Normal Host Cells Results in Severe Autoimmune Diease." *J. Exp. Med*. 191.5(2000):795-804.
Majeti et al. "Identification of a Hierarchy of Multipotent Hematopoietic Progenitors in Human Cord Blood." *Cell Stem Cell*. 1.6(2007):635-645.
Maimqvist. "Biospecific Interaction Analysis Using Biosensor Technology." *Nature*. 361.6408(1993):186-187.
Mammoto et al. "Mechanical Control of Tissue and Organ Development." *Development*. 137.9(2010):1407-1420.
Manavski et al. "Vascular Niche Controls Organ Regeneration." *Clin Res*. 114.17(2014):1077-1079.
Mansoor et al. "Engineering T Cells for Cancer Therapy." *Br. J. Cancer*. 93.10(2005):1085-1091.
Masedunskas et al. "Role for the Actomyosin Complex in Regulated Exocytosis Revealed by Intravital Microscopy." *PNAS*. 103. 33(2011):13552-13557.
McDonald et al. "Early Fracture Callus Displays a Smooth Muscle-Like Viscoelastic Properties Ex Vivo: Implications for Fracture Healing." *J. Orthop. Res*. 27.11(2009):1508-1513.
McKinnon et al. "Biophysically Defined and Cytocompatible Covalently Adaptable Networks as Viscoelastic 3D Cell Culture Systems." *Adv. Mater*. 26.6(2014):865-872.
McWhorter et al. "Modulation of Macrophage Phenotype by Cell Shape." *PNAS*. 110.43(2013):17253-17258.
Melief et al. "Immunotherapy of Established (Pre)Malignant Disease by Synthetic Long Peptide Vaccines." *Nat. Rev. Cancer*. 8(2008):351-360.
Merkel et al. "Using Mechanobiological Mimory of Red Blood Cells to Extend Circulation Times of Hydrogel Microparticles." *PNAS*. 108.2(2011):586-591.
Metters et al. "Fundamental Studies of Biodegradable Hydrogels as Cartilage Replacement Materials." *Biomed. Sci. Instrum*. 35(1999):33-38.
Milikovic et al. "Chondrogenesis, Bone Morphogenetic Protein-4 and Mesenchymal Stem Cells." *Osteoarthritis Cartilage*. 16(2008):1121-1130.
Miller et al. "Melanoma." *N. Engl. J. Med*. 355.1(2006):51-65.
Miralles et al. "Actin Dynamics Control SRF Activity by Regulation of its Coactivator MAL." *Cell*. 11.3(2003):329-342.
Moiinari et al. "Modification of Surface Membrane Antigens by Trypsin." *Proc. Soc. Exp. Biol. Med*. 148.4(1975):991-994.

(56) References Cited

OTHER PUBLICATIONS

Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Muralidharan-Chari et al. "ARF6-Regulated Shedding of Tumor Cell-Derived Plasma Membrane Microvesicles." *Curr. Biol.* 19.22(2009):1875-1885.
NCBI Accession No. NM_001561.5, Mar. 6, 2014.
NCBI Accession No. NM_004448.3, Apr. 23, 2014.
NCBI Accession No. NM_005018.2, Apr. 27, 2014.
NCBI Accession No. NM_181780.3, Jan. 27, 2014.
NCBI Accession No. NP_001193, May 3, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_005009.2, Apr. 27, 2014.
NCBI Accession No. NP_861445.3, Jan. 27, 2014.
Nichol et al. "Cell-Laden Microenginnered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The $\alpha 6\beta 4$ Integrin is a Receptor for Both Lamin and Kalinin." *Exp. Cell Res.* 211.2(1994):360-367.
Osunkoya et al. "Synthesis and Fate of Immunological Surface Receptors on Cultured Burkit Lymphome Cells." *Int. J. Cancer.* 4.2(1969):159-165.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.6(2008):599-606.
Pardoll. "The Blockade of Immune Checkpoints in Cancer Immunotheraphy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.
Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Pawlaczyk et al. "Age-Dependent Biomechanical Properties of the Skin." *Postepy. Dermatol. Alergol.* 30.5(2013):302-306.
Pek et al. "The Effect of Matrix Striffness on Mesenchymal Stem Cell Differentiation in a 3D Thixotropic Gel." *Biomater.* 31.3(2010):385-391.
Pena et al. "Effecys of TGF-$\beta$ and TGF-$\beta$ Neutralizing Antibodies on Fibroblast-Induced Collagen Gel Contraction: Implications for Proliferative vitroretinpathy." *Invest. Ophthalmol. Vis. Sci.* 35.6(1994):2804-2808.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Pinho et al. "PDGFR$\alpha$ and CD51 Mark Human Nestin+ Sphere-Forming Mesenchymal Stem Cells Capable of Hematopoietic Progenitor Cell Expansion." *J. Exp. Med.* 210.7(2013):1351-1367.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.
Raeber et al. "Molecualry Engineered PEG Hydrogels: A Novel Model System for Proteolyically Mediated Cell Migration." *Biophys. J.* 89.2(2005):1374-1388.
Ramón-Azcón et al. "Gelatin methacrylate as Promising Hydrogel for 3D Microscale Organization and Proliferation of Dielectroretically Patterned Cells." *Lab on a Chip.* 12.16(2012):2959-2969.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Roccaro et al. "BM Mesenchymal Stromal Cell-Derived Exosomes Facilitate Multiple Myeloma Progression." *J. Clin. Invest.* 123.4(2013):1542-1555.
Rodriguez et al., "Minimal Self" Peptides that Inhibit Phagocytic Clearence and Enhance Delivery of Nanoparticles. *Science.* 339.6122(2013):971-975.
Saccheti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Scheel et al. "Toll-Like Receptor-Dependent Activation of Several Human Blood Cell Types by Protamine Condensed mRNA." *Eur. J. Immunol.* 35(2005):1557-1566.
Schofield. "The Relationship Between the Spleen Colony-Forming Cell and the Haemopoietic Stem Cell." *Blood. Cells.* 4.1-2(1978):7-26.
Schwartz, "Integrins and Extracellular Matrix in Mechanotransduction." *Cold Spring Harb. Perspect. Biol.* 2.12(2010):a005066.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shi et al. "Granulocyte-Macrophage Colony-Stimulating Factor (GM-CSF) and T-Cell Responses: What we do and don't know." *Cell Res.* 16.2(2006):126-133.
Shin et al. "Concentrate Forces Sustain and Polarize Hematopoiesis from Stem and Progenitor Cells." *Cell Stem Cell.* 14.1(2014):81-99.
Shin et al. "Lamins Regulate Cell Trafficking and Lineage Maturation of Adult Human Hematopoetic Cells." *PNAS.* 110.47(2013):18892-18897.
Shin et al. "Myonsis-II Inhibition and Soft 2D Matrix Maximize Multinucleation and Cellular Projections Typical of Platelet-Producing Megakaryocytes." *PNAS.* 108.28(2011):11458-11463.
Siegwart et al. "Synthesis Characterization, and in vitro Cell Culture Viability of Degradable Poly(N-isopropylacrylamide-co-5,6-benzo-2-methylene-1,3-dioxepane)-Based Polymers and Crosslinked Gels." *J. Biomed. Mater. Res. A.* 87.2(2008):345-358.
Silva et al. "Effects of VEGF Temporal and Spatial Presentation on Angiogenesis." *Biomaterials.* 31.6(2010):1235-1241.
Singer et al. "Cutaneous Wound Healing." *N. Engl. J. Med.* 341.10(1999):738-746.
Solon et al. "Fibroblast Adaptation and Stiffness Matching to Soft Elastic Substrates." *Biophys. J.* 93.12(2007):4453-4461.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter.* 8(2012):2398-2404.
Sun et al. "Highly Stretchable and Tough Hydrogels." *Nature.* 489.7414(2012):133-136.
Suri et al. "Photopatterned Collagen-Hyaluronic Acid Interpenetrating Polymer Network Hydrogels." *Acta Biomater.* 5.7(2009):2385-2397.
Swift et al. "Nuclear Lamin-A Scales with Tissue Stiffness and Enhances Matrix-Directed Differentiation." *Science.* 341.6149(2013):1240104.
Syed et al. "Stem Cell Therapy Market." *Nat. Rev. Drug Discov.* 12.3(2013):185-186.
Tabata et al. "Enhanved Vascularization and Tissue Granulation by Basic Fibroblast Growth Factor Imprenated in Gelatin Hydrogels." *J. Control Release.* 31.2(1994):189-199.
Tannous. "Gaussia Luciferase Reporter Assay for Monitoring Biological Processes in Culture and in vivo." *Nat. Protoc.* 4.4(2009):582-591.

(56) References Cited

OTHER PUBLICATIONS

Thomas et al. "Intravenous Infusion of Bone Marrow in Patients Receiving Radiation and Chemotherapy." *N. Engl. J. Med.* 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med.* 190.11(1999):1669-1678.
Tong et al. "Engineering Interpenetrating Network Hydrogels as Biomimetic Cell Niche with Independently Tunable Biochemical and Mechanical Properties." *Biomater.* 35.6(2014):1807-1815.
Trappmann et al. "Extracellular-Matrix Tethering Regulates Stem-Cell Fate." *Nat. Mater.* 11.7(2012):642-649.
Trappmann et al. "How Cells Sense Extracellular Matrix Stiffness: A Material's Perspective." *Curr. Opin. Biotechnol.* 24.5(2013):948-953.
Urgate et al. "Notch Signaling Enhances Osteogenic Differentiation While Inhibiting Adipogenesis in Primary Human Bone Marrow Stromal Cells." *Exp. Hematol.* 37(2009):867-876.
Uhlenbruck. "Action of Proteolytic Enzymes on the Human Erthrocyte Surface." *Nature.* 190(1961):181.
Ulrich et al. "Probing Cellular Mechanobiology in Three-Dimensional Culture with Collagen-Agarose Matrices." *Biomater.* 31.7(2010):1875-1884.
UniProtKB/Swiss-Prot Accession No. p02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
van der Bruggen et al. "T Cell-Defined Tumor Antigens." *Cancer Immunity.* (2013). Http:www.cancerimmunity.org/peptide.
Venturoni et al. "Investigations into the Polymorphism of Rat Tail Fibrils Using Atomic Force Microscopy." *Biochem. Biophys. Res. Commun.* 303.2(2003):508-513.
Vincent et al. "Stem Cell Differentiation: Post-Degradation Forces Kick in." *Nat. Mater.* 12.5(2013):384-386.
Vogel et al. "Local Force and Geometry Sensing Regulate Cell Functions." *Nat. Rev. Mol. Cell Biol.* 7.4(2006):265-275.
Wang et al. "Mechanotransduction at a Distance: Mechanically Coupling the Extracellular Matric with Nucleus." *Nat. Rev. Cell. Biol.* 10.1(2009):75-82.
Wang-Gillam et al. "A Phase I Study of IMP321 and Germcitabine as the Front-Line Therapy in Patients with Advanced Pancreatic Adenocarcinoma." *Invest. New Drugs.* 31.3(2013):707-713.
Warner et al. "Cydooxygenases: New Forms, New Inhibitors, and Lessons from the Clinic." *FASEB J.* 18.7(2004):790-804.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res.* 30(1963):331-338.

Wen et al. "Mechanically Robust Gelatin-Alginate IPN Hydrogels by a Combination of Enzymatic and Ionic Crosslinking Approaches." *Macromol. Mater. Eng.* 299(2013):504-513.
Wieland et al. "Engineering Molecular Circuits Using Synthetic Biology in Mammalian Cells." *Annu. Rev. Chem. Biomol. Eng.* 3(2012):209-234.
Wipff et al. "Myofibroblast Contraction Activates Latent TGF-β1 from the Extracellular Matrix." *J. Cell Biol.* 179.6(2007):1311-1323.
Wong et al. "Focal Adhesion Kinase Links Mechanical Force to Skin Fibrosis via Inflammatory Signaling." *Nat. Med.* 18.1(2011):146-152.
Wong et al. "Mechanical Force Prolongs Acute inflammation via T-Cell-Dependent Pathways During Scar Formation." *FASEB. J.* 25.12(2011):4498-4510.
Wong et al. "Pushing Back: Wound Mechanotransduction in Repair and Regeneration." *J. Invest. Dermatol.* 131.11(2011):2186-2196.
Wozniak et al. "Mechantransduction in Development: A Growing Role for Contractillity." *Nat. Rev. Mol. Cell Biol.* 10.1(2009):34-43.
Yeung et al. "Effects of Substrate Stiffness on Cell Morphology, Cytoskeletal Structure, and Adhesion." *Cell Motil. Cytoskeleton.* 60.1(2005):24-34.
Yoo et al. "Bio-inspired, Bioengineered and Biomimetic Drug Delivery Carriers." *Nat. Rev. Drug Discov.* 10.7(2011):521-535.
Yoon, "Hidden Markov Models and their Applications in Biological Sequence Analysis." *Curr. Genomics.* 10.6(2009):402-415.
Young et al. "Gelatin as a Delivery Vehicle for the Controlled Release of Bioactive Molecules." *J. Control. Release.* 109.1-3(2005):256-274.
Zemel et al. "Optimal Matrix Rigidity for Stress Fibre Polarization in Stem Cell." *Nat. Phys.* 6.6(2010):468-473.
Zhang et al. "A Tension-Induced Mechanostransduction Pathway Promotes Epithelial Morphogenesis." *Nature.* 471.7336(2011):99-103.
Zhang et al. "Talin Depletion Reveals Independence of Initial Cell Spreading from Integrin Activation and Traction." *Nat. Cell Biol.* 10.9(2008):1062-1068.
Zhao et al. "Stress-Relaxation Behavior in Gels with Ionic and Covalent Crosslinks." *J. Appl. Phys.* 107.6(2010):63509.
"Antigens and Receptors." *Immunology.* Doan et al., eds. Philadelphia: Wolters Kluwer/Lippincott Williams & Wilsons. (2008):11-23.
"Wound Management: Past, Present, and Future." *Clinicians' Pocket Guide to Chronic Wound Repair.* Mulder et al., eds. Springhouse, PA: Springhouse Corporation. (1998):85-90.
Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agrawal et al. "Cutting Edge: Different Toll-Like Receptor Agonists Instruct Dendritic Cells to Induce Distint Th Responses via Differential Modulation of Extracellular Signal-Regulated Kinase-Mitogen-Activated Protein Kinease and c-Fos." *J. Immunol.* 171.10(2003):4984-4989.
Akira et al. "Pathogen Recognition and Innate Immunity." *Cell.* 124.4(2006):783-801.
Akira et al. "Toll-Like Receptors: Critical Proteins Linking Innate and Acquired Immunity." *Nat. Immunol.* 2.8(2001):675-680.
Aldhous. "Print Me a Heart and Set of Arteries." *New Scientist.* 2547(2006):19.
Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
Ali et al. "Converging Cell Therapy with Biomaterials." *Cell Transplantation from Laboratory to Clinic.* Burlington, MA: Elsevier, Inc. (2006):591-609.
Ali et al. "In situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Ali et al. "Sustained GM-GSF and PEI Condensed pDNA Presentation Increases the Level and Duration of Gene Expression in Dendritic Cells." *J. Control. Release.* 132.3(2008):273-278.

(56) References Cited

OTHER PUBLICATIONS

Allen et al. "Regulation of Satelite Cells During Skeletal Muscle Growth and Development." *Proc. Soc. Exp. Biol. Med.* 194.2(1990):81-86.
Allen et al. "Regulation of Skeletal Muscle Satelite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11(2001):2025-2029.
Alsberg et al. "Engineering Growing Tissues." *PNAS.* 99.18(2002):12025-12030.
Alsberg et al. "Regulating Bone Formation via Controlled Scaffold Design." *J. Dent. Res.* 82.11(2003):903-908.
Anderson et al. "Biomaterial Microarrays: Rapid, Microscale Screening of Polymer-Cell Interaction." *Biomaterials.* 26.23(2005):4892-4897.
Anderson et al. "Nanoliter-Scale Synthesis of Arrayed Biomaterials and Application to Human Embryonic Stem Cells." *Nat. Biotechnol.* 22.7(2004):863-866.
Anderson et al. "The NOD Mouse: A Model of Immune Dysregulation." *Annu. Rev. Immunol.* 23(2005):447-485.
Anderson. "A Role for Nitric Oxide in Muscle Repair: Nitric-Oxide-Mediated Activation of Muscle Satelite Cells." *Mol. Biol. Cell.* 11(2000):1859-1874.
Arany et al. "At the Edge of Translation—Materials to Program Cells for Directed Differentiation." *Oral Dis.* 17.3(2011):241-251.
Atala et al. "Endoscopic Treatment of Vesicoureteral Reflux with a Chondrocyte-Alginate Suspension." *J. Urol.* 152(1994):641-643.
Augst et al. "Alginate Hydrogels as Biomaterials." *Macromol. Biosci.* 6(2006):623-633.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Bachem et al. "Superior Antigen Cross-Presentation and XCR1 Expression Define Human CD11c+CD141+ Cells as Homologues of Mouse CD8+ Dendritic Cells." *J. Exp. Med.* 207.6(2010):1273-1281.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Opthalmology.* 114.5(2007):855-859.
Balakrishna et al. "Structural Correlates of Antibacterial and Membrane-Permeabilizing Activities in Acylpolyamines." *Antimicrob. Agents Chemother.* 50.3(2006):852-861.
Banchereau et al. "Demdritic Cells and the Control of Immunity." *Nature.* 392.6673(1998):245-252.
Bar-Cohen et al. "Electroactive Polymer Actuators and Sensors." *MRS Bullet.* 33.3(2008):173-181.
Bar-Or et al. "Induction of Antigen-Specific Tolerance in Multiple Sclerosis after Immunization with DNA Encoding Myelin Basic Protein in a Randomized, Placebo-Controlled Phase ½ Trail." *Arch. Neurol.* 64.10(2007):1407-1415.
Barbero et al. "Growth Factor Supplemented Matrigel Improves Ectopic Skeletal Muscle Formation—A Cell Therapy Approach." *J. Cell. Physiol.* 186(2001):183-192.
Barrio et al. "A Two-Dimensional Numerical Study of Spatial Pattern Formation in Interacting Turing Systems." *Bull. Math. Biol.* 61.3(1999):483-505.
Bates. "Improved Muscle Regeneration by Combining VEGF With IGF1." *Regen. Med.* 5.6(2010):853-854.
Beaucage et al. "The Functionalization of Oligonucleotides Via Phosphoramide Derivatives." *Tetrahedron.* 49.10(1993):1925-1963.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.

Beebe et al. "Functional Hydrogel Structures for Autonomous Flow Control Inside Microfluidic Channels." *Nature.* 404(2000):588-590.
Bekiari et al. "Study of Poly(N,N-dimethylacrylamide)/CdS Nanocomposite Organic/Inorganic Gels." *Langmuir.* 20.19(2004):7972-7975.
Bischoff. "Proliferation of Muscle Satellite Cells on Intact Myofibers in Culture." *Dev. Biol.* 115.1(1986):129-139.
Blanas et al. "Induction of Autoimmune Diabetes by Oral Administration of Autoantigen." *Science.* 274.5293(1996):1707-1709.
Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.
Bohl et al. "Role of Synthetic Extracellular Matrix in Development of Engineered Dental Pulp." *J. Biomater. Sci. Polym.* Ed. 9.7(1996):749-764.
Bonauer et al. "MicroRNA-92a Controls Angiogenesis and Functional Recovery of Ischemic Tissues in Mice." *Science.* 324.5935(2009):1710-1713.
Boontheekul et al. "Regulating Myoblast Phenotype Through Controlled Gell Stiffness and Degradation," *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Degradation of Partially Oxidized Alginate and its Potential Application for Tissue Engineering." *Biotechnol. Prog.* 17.5(2001):945-950.
Bouhadir et al. "Synthesis of Cross-Linked Poly(aldehyde guiuronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brinkman et al. "Neutrophil Extracellular Traps Kill Bacteria." *Science.* 303.5663(2004):1532-1535.
Brouwers et al. "Can the Growth Factors PTHiP, Ihh and VEGF, Together Regulate the Development of a Long Bone?" *J. Biomech.* 39.15(2006):2774-2782.
Bryant et al. "Photo-Patterning of Porous Hydrogels for Tissue Engineering." *Biomater.* 28.19(2007):2978-2986.
Burdick et al. "Stimulating of Neurite Outgrowth by Neurotrophins Delivered From Degradable Hydrogels." *Biomater.* 27.3(2006):452-459.
Calvert et al. "Electroacive Polymer Gels." *Electroactive Polymer (EAP) Actuators as Artificial Muscle: Reality, Potential, and Challenges.* Bar-Cohen. ed. Bellingham, WA: Spie Press (2004):151-170.
Calvert. "Gel Sensors and Actuators." *MRS Bullet.* 33.3(2008):207-212.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmellet. "Mechanisms of Angiogenesis and Arteriogenesis." *Nat. Med.* 6.3(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.

(56) References Cited

OTHER PUBLICATIONS

Choi. "Replacement Organs, Hot Off the Press." *New Scientist.* 177.2379(2003):16.

Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.

Clauss et al. "Interstitial Transport of Rabbit and Sheep Antibodies in Normal and Neoplastic Tissues." *Cancer Res.* 50.12(1990):3487-3492.

Cohen et al. "Controlled Delivery Systems for Proteins Based on Poly(Lactic/Glycolic Acid) Microspheres." *Pharm. Res.* 8.6(1991):713-720.

Conboy et al. "The Regulation of Notch Signaling Controls Satellite Cell Activation and Cell Fate Determination in Postnatal Myogenesis." *Dev. Cell.* 3.3(2002):397-409.

Conconi et al. "In vitro and in vivo Evaluation of Acellular Diaphramatic Matrices Seeded with Muscle Precusors Cells and Coated with VEGF Silica Gel to Repair Muscle Defect of the Diaphram." *J. Biomed. Mater. Res.* 89A.2(2009):304-316.

Conn et al. "Purification of a Glycoprotein Vascular Endothelial Cell Mitogen From a Rat Glioma-Derived Cell Line." *PNAS.* 87.4(1990):1323-1327.

Cooper et al. "Extended Amplification In Vitro and Replicative Senescence: Key Factors Implicated in the Success of Human Myoblast Transplantation." *Hum. Gene. Ther.* 14(2003):1169-1179.

Cornelison et al. "Single-Cell Analysis of Regulatory Gene Expression in Quiescent and Activated Mouse Skeletal Muscle Satellite Cells." *Dev. Biol.* 191.2(1997):270-283.

Cornelison et al. "Syndecan-3 and Syndecan-4 Specifically Mark Skeletal Muscle Satellite Cells and Are Implicated in Satellite Cell Maintenance and Muscle Regeneration." *Dev. Biol.* 239.1(2001):79-94.

Coulson et al. "Flow of Fluids through Granular Beds and Packed Columns." *Chemical Engineering.* New York: Pergamon Press. 2(1978):125-171.

Crameri et al. "Improved Green Fluorescent Protein by Molecular Evolution Using DNA Shuffling." *Bat. Biotechol.* 14.3(1996):315-319.

Cullen et al. "Investigation of Vascular Endothelial Growth Factor Effects on Pulmonary Endothelial Monolayer Permability and Neutrophil Transmigration." *Gen. Pharmacol.* 35.3(2000):149-157.

Curiel et al. "Tumor Immunotheraphy: Inching Toward the Finish Line." *J. Clin. Invest.* 109.3(2002):311-312.

D'Amico et al. "The Early Progenitors of Mouse Dendritic Cells and Plasmacytoid Predendritic Cells are within the Bone Marrow Hemopoietic Precursors Expressing FIt3." *J. Exp. Med.* 198.2(2003):293-303.

Dar et al. "Optimization of Cardiac Cell Seeding and Distribution in 3D Porous Alginate Scaffolds." *Biotechnol. Bioeng.* 80(2002):305-312.

Daro et al. "Polyethlene Glycomodified GM-CSF Expands CD11bhighCD11chigh but not CD11blowCD11chigh Murine Dendritic Cells In Vivo: A Comparative Analysis with FIt3 Ligand." *J. Immunol.* 165.1(2000):49-58.

De Temmernan et al. "Particulate Vaccines: On the Quest for Optimal Delivery and Immune Response." *Drug Disc. Today.* 16.13/14(2011):569-582.

de Haan et al. "CD8+ by not CD8− Dendritic Cells Cross-Prime Cytotoxic T Cells in Vivo." *J. Exp. Med.* 192.12(2000):1685-1696.

Dennis et al. "Excitability and Contractility of Skeletal Muscle Engineered From Primary Cultures and Cell Lines." *Am. J. Physiol. Cell Physiol.* 280(2001):C288-C295.

Dennis et al. "Excitability and Isometric Contractile Properties of Mammalian Skeletal Muscle Contructs Engineered in vitro." *In Vitro Cell Dev. Biol. Anim.* 36.5(2000):327-335.

Dieu et al. "Selective Recruitment of Immature and Mature Dendritic Cells by Distint Chemokines Expressed in Different Anatomic Sites." *J. Exp. Med.* 188.2(1988):373-386.

Doan et al. "Subcellular Localization of a Sporulation Membrane Protein is Achieved Through a Network of Interactions Along and Across the Septum." *Mol. Microbiol.* 55.6(2005):1767-1781.

Dor et al. "Making Vascular Networks in the Adult: Branching Morphogenesis Without a Roadmap." *Trends Cell Biol.* 13.3(2003):131-136.

Dranoff et al. "Vaccination with Irrafiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.

Dranoff. "Cytokines in Cancer Pathogenesis and Cancer Therapy." *Nat. Rev. Cancer.* 4.1(2004):11-22.

Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.

Eghoim et al. "Peptide Nucleic Acids (PNA). Oligonucleotide Analogues with an Achiral Peptide Backbone." *J. Am. Chem. Soc.* 114.5(1992):1895-1897.

Egholm et al. "PNA Hybridizes to Complementary Oligonucleotides Obeying the Watson-Crick Hydrogen-Bonding Rules." *Nature.* 365.6446(1993):566-568.

Ehrbar et al. "Entothelial Cell Proliferation and Progenitor Maturation by Fibrin-Boud VEGF Variants with Differential Susceptibilites to Local Cellular Activity." *J. Control. Release.* 101(2004):93-109.

Elselt et al. "Porous Carriers for Biomedical Applications Based on Alginate Hydrogels." *Biomat.* 21.19(2000):1921-1927.

El-Backly et al. "Regeneration of Dentine/Pulp-Like Stem Cell/Poly(Lactic-Co-Glycolic) Acid Scaffold Construct in New Zealand White Rabbits." *Aust. Endod. J.* 34.2(2008):52-67.

Eldar et al. "Eluicidating Mechanisms Underlying Robustness of Morphogen Gradients." *Curr. Opin. Genet. Dev.* 14.4(2004):435-439.

Eldar et al. "Robustness of BMP Morphogen Gradient in *Drosophila* Embryonic Patterning." *Nature.* 419.6904(2002):304-308.

Eldar et al. "Self-Enhanced Ligand Degradation Underlies Robustness of Morphogen Gradients." *Dev. Cell.* 5.4(2003):635-646.

Engler et al. "Matrix Elasticity Directs Stem Cell Lineage Specification." *Cell.* 126.4(2006):677-689.

Ennett et al. "Temporally Regulated Delivery of VEGF in vitro and in vivo." *J. Biomed. Mater. Res. A.* 79.1(2006):176-184.

Faissner et al. "Boudaries and Inhibitory Molecules in Developing Neural Tissues." *Glia.* 13.4(1995):233-254.

Falsey et al. "Peptide and Small Molecule Microarray for High Throughput Cell Adhesion and Functional Assays." *Bioconjug. Chem.* 12.3(2001):346-353.

Farrar et al. "T Helper Subset Development: Roles of Instruction, Selection, and Transcription." *J. Clin. Invest.* 109.4(2002):431-435.

Ferrara et al. "Angiogenesis as a Therapeutic Target." *Nature.* 438.7070(2005):967-974.

Ferrara et al. "Discovery and Development of Bevacizumab, an Anti-VEGF Antibody for Treating Cancer." *Nat. Rev. Drug Discov.* 3.5(2004):391-400.

Fischer et al. "A Brilliant Monomeric Red Fluorescent Protein to Visualize Cytoskeleton Dynamics in *Dictyostellum.*" *FEBS Lett.* 577.1-2(2004):227-232.

Fischer et al. "Visualizing Cytoskeleton Dynamics in Mammalian Cells Using a Humanized Variant of Monomeric Red Fluorescent Protein." *FEBS Lett.* 580.10(2006):2495-2502.

Folkman. "Angiogenesis." *Annu. Rev. Med.* 57(2006):1-18.

Fonseca et al. "Capitalizing on the Immunogenicity of Dying Tumor Cells." *Clin. Cancer Res.* 14.16(2008):1603-1608.

Fontaine et al. "Surgical Treatment of Peripheral Circulation Disorders." *Helv. Chir. Acta.* 21.56(1954):499-533. (German Original, No English Translation Available).

Fox. "Management of Worsening Multiple Sclerosis with Mitoxantrone: A Review." *Clin. Ther.* 28.4(2006):461-474.

Friedrich et al. "Promoter Traps in Embryonic Stem Cells: A Genetic Screen to Idenitfy and Mutate Developmental Genes in Mice." *Genes Dev.* 5(1991):1513-1523.

Fukushima et al. "The Use of an Antibibrosis Agent to Improve Muscle Recovery After Laceration." *Am. J. Sports Med.* 29.4(2001):394-402.

(56) References Cited

OTHER PUBLICATIONS

Gamvrellis et al. "Vaccines that Facilitate Antigen Entry into Dendritic Cells." *Immunol. Cell Biol.* 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB311818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAI44040, Mar. 18, 2009.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. EF064765.1, Nov. 13, 2006.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenesis Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Glasbey et al. "Image Analysis and Three-Dimensional Modelling of Pores in Soil Aggregates." *Eur. J. Soii Sci.* 42.2(1991):479-486.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Ololarynot. Head Neck Surg.* 130.10(2004):1191-1196.
Gros et al. "A Common Somitic Orgin for Embryonic Muscle Progenitors and Satellite Cells." *Nature.* 435(2005):954-958.
Guilberg et al. "Extracellular Matrix and Its Receptors During Development." *Int. J. Dev. Biol.* 39(1995):845-854.
Gupta et al. "Magnetically Controlled Targeted Micro-Carrier Systems." *Life Sci.* 44.3(1989):175-186.
Gussoni et al. "Dystrophin Expression and in the *mdx* Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabillitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotheraphy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Heath. "Cells for Tissue Engineering." *Trends Biotechnol.* 18.1(2006):17-19.
Helm et al. "Synergy Between Interstilial Flow and VEGF Directs Capillary Morphogenesis in vitro Through a Gradient Amplification Mechanism." *PNAS.* 102.44(2005):15779-15784.

(56) References Cited

OTHER PUBLICATIONS

Henry et al. "The VIVA Trial: Vascular Endothelial Growth Factor in Ischemia for Vascular Angiogenesis" *Circulation.* 107.10(2003):1359-1365.
Hermanson. *Bioconjugate Techniques.* New York: Academic Press. (1996): 152-185.
Heslop et al. "Transplanted Primary Neonatal Myoblasts can Give Rise to Functional Satellite Cells as Identified Using the Myf5nlacZl+ Mouse." *Gene Ther.* 8(2001):778-783.
Hildner et al. "*Batf3* Deficiency Reveals a Critical Role for CD8α+ Dendritic Cells in Cytotoxic T Cell Immunity." *Science.* 322. 5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Mcroporous Scaffold Architecture, Peptide, HGF/FGF and Myoblast Incorporation Enhance Myogenesis." *IADR/AADR/CADR 83rd General Session* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998): 13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Horsley et al. "IL-4 Acts as Myoblast Recruitment Factor During Mammalian Muscle Growth." *Cell.* 113.4(2003):483-494.
Hsiong et al. "Differentiation Stage Alters Matrix Control of Stem Cells." *J. Biomed. Mater. Res. Part A.* 8(2007):145-156.
Huang et al. "Fabrication and in vitro Testing Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene. Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tecj.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Ishihara et al. "Roles of Bradykinin in Vascular Permeability and Angiogenesis in Solid Tumor." *Int. Immunopharmacol.* 2.4(2002):499-509.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).
Jain. "Molecular Regulation of Vessel Maturation." *Nat. Med.* 9.6(2003):685-693.
Jain. "The Manufacturing Techniques of Various Drug Loaded Biodegradable Poly(lactide-*co*-glycolide) (PLGA) Devices." *Biomater.* 21.23(2000):2475-2490.
Jankovic et al. "In the Absence of IL-12, CD4+ T Cell Responses to Intracellular Pathogens Fail to Default to a Th2 Pattern and are Host Protective in a IL-10-/- Setting." *Immunity.* 16.3(2002):429-439.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, Number and Spacing of Primordia." *Development.* 126.22(1999):4997-5009.
Jinushi et al. "Enhancing the Clinical Activity of Granulocyte-Macrophage Colony-Stimulating Factor-Screening Tumor Cell Vaccines." *Immunol. Rev.* 222(2008):287-298.

Jinushi et al. "MFG-R8-Mediated Uptake of Apoptoic Cells by APCs Links the Pro- and Antiinflammatory Activitiesof GM-CSF." *J. Clin Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Juntanon et al. "Electrically Controlled Release of Sulfosalicyclic Acid from Crosslinked Poly(Vinyl Alcohol) Hydrogel." *Int. J. Pharm.* 356(2008):1-11.
Kanzler et al. "Therapeutic Targeting of Innate Immunity with Toll-Lke Receptor Agaonists and Antagonists." *Nat. Med.* 13.5(2007):552-559.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.1-2(1999):279-287.
Khowniumet al. "Novel Endotoxin-Compounds with Terephthaldehyde-bis-guanyllhydrazone Scaffolds." *Bioorg. Med. Chem. Lett.* 16(2006):1305-1308.
Kim et al. "An Overview of Cartilage Tissue Engineering." *Yonsei Med. J.* 41.6(2000):766-773.
Kim et al. "The Effect of VEGF on the Myogenic Differentiation of Adipose Tissue Derived Stem Cells Within Thermosensitive Hydrogel Matrices." *Biomaterials.* 31.6(2010):1213-1218.
Kinoshita et al. "Successive injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klinman. "Immunotherapeutic Uses of CpG Oligodeoxynucleotides." *Nat. Rev. Immunol.* 4.4(2004):249-258.
Kondo et al. "A Reaction-Diffusion Wave on the Skin of the Marine Angelfish *Pomacanthus.*" *Nature.* 376(2002):765-768.
Kong et al. "Controlling Degradation of Hydrogels via the Size of Crosslinked Junctions." *Adv. Mater.* 16.21(2004):1917-1921.
Kong et al. "Controlling Rigidity and Degradation of Alginate Hydrogels via Molecular Weight Distribution." *Biomacromolec.* 5.5(2004):1720-1727.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Kong et al. "Designing Alginate Hydrogels to Maintain Viability of Immobilized Cells." *Biomat.* 24.22(2003):4023-4029.
Kong et al. "Non-Viral Gene Delivery Regulated By Stiffness of Cell Adhesion Substrates." *Nat. Mater.* 4(2005):406-410.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapsharmaceutica.com/ExpoAAPS09/CC/forms/attendee/index.aspx?contetn=sessionInfo&sessionId=2716.
Kumamoto et al. "Induction of Tumor-Specific Protective Immunity by in situ Langerhans Cell Vaccine." *Nat. BioTechnol.* 20.1(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kwon et al. "Electrically Erodible Polymer Gel for Controlled Release of Drugs." *Nature.* 354(1991):291-293.
Kwon et al. "In vivo Targeting Dendritic Cells for Activation of Cellular Immunity Using Vaccine Carriers Based on pH-Responsive Microparticles." *PNAS.* 102.51(2005):18264-18268.
Lagenkamp et al. "Kinetics of Dendritic Cell Activation: Impact on Priming of TH1, TH2 and Nonpolarized T Cells." *Nat. Immunol.* 1.4(2000):311-316.

(56) References Cited

OTHER PUBLICATIONS

Langer et al. "Tissue Engineering." *Science.* 260(1993):920-926.
Lanzavecchia et al. "Regulation of T Cell Immunity by Dendritic Cells." *Cell.* 106.3(2001):263-266.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8α+ DCs and Human BDCA3+ DCs are Major Producers of IFN-λ in Response to Poly IC." *J. Exp. Med.* 207.12(2010):2703-2717.
Leach et al. "Coating of VEGF-Releasing Scaffolds with Bioactive Glass for Angiogenesis and Bone Regenertion." *Biomater.* 27.17(2006):3249-3255.
Lee et al. "Hydrogel Formation via Vell Crosslinking." *Adv. Mat.* 15.21(2003):1828-1832.
Lee et al. "Hydrogels for Tissue Engineering." *Chem. Rev.* 101.7(2001):1869-1879.
Lefaucheur et al. "The Cellular Events of Injured Muscle Regeneration Depend on the Nature of the Injury." *Neuomusc. Disorders.* 5.6(1995):501-509.
Lensch et al. "Scientific and Clinical Opportunites for Modeling Blood Disorders With Embryonic Stem Cells." *Blood.* 107.7(2006):2605-2612.
Leor et al. "Cells, Scaffolds, and Molecules for Myocardial Tissue Engineering." *Pharmacol. Therapeutics.* 105(2005):151-163.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Letsinger et al. "Phosporamidate Analogs of Oligonucleotides." *J. Org. Chem.* 35.11(1970):3800-3803.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li, "TNF-α is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu et al. "Nanostructed Materials Designed for Cell Binding and Transduction." *Biomacromolecules.* 2.2(2001):362-368.
Liu. "Dendritic Cell Subsets and Lineages, and Their Functions in Innate and Adaptive Immunity." *Cell.* 106.3(2001):259-262.
Lu et al. "Muscle-Derived Stem Cells Seeded Into Acellular Scaffolds Develop Calcium-Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292.5520(2001):1389-1394.
Lutolf et al. "Repair of Bone Defects Using Synthetic Mimetics of Collagenous Extracellular Matrices." *Nat. Biotechnol.* 21.5(2003):513-518.
López et al. "Magnetic Applications of Polymer Gels." *Macromol. Symp.* 166.1(2001):173-178.
Mach et al. "Differences in Dendritic Cells Stimulated in Vivo by Tumors Engineered to Secrete Granulocyte-Macrphage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.

Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Martinsen et al. "Alginate as Immobilization Material." *Biotech. Bioeng.* 33.1(1989):79-89.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Massia et al. "An RGD Spacing of 440 nm is Sufficient for Integrin αvβ3-Mediated Fibroblast SPreading and 140 nm for Focal Contact and Stress Fiber Formation." *J. Cell. Biol.* 114.5(1991):1089-1100.
Matthew et al. "Subperiostral Behavior of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-β Superfamily Member." *Nature.* 387(1997):83-90.
Meier et al. "Peptide Nucleic Acids (PNAs)—Unusal Properties of Noionic Oligonucleotide Analogues" *Angew. Chem. Int. Ed.* 31.8(1992):1008-1010.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):256-258.
Menetry et al. "Suturing Versus Immbolization of a Muscle Laceration: A Morphological and Functional Study in a Mouse Model." *Am. J. Sports Med.* 27.2(1999):222-229.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Meyer et al. "Clinical Investigations of Toll-Like Receptor Agonists." *Expert. Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Miller et al. "Lipopolysaccharide Sequestrants: Structural Correlates of Activity and Toxicity in Novel Acylhomospermins." *J. Med. Chem.* 48(2005):2589-2599.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Miyata et al. "Biomolecule-Sesitive Hydrogels." *Adv. Drug Deliv. Rev.* 54.1(2002):78-98.
Mohan et al. "Novel Porous, Polysaccharide Scaffolds for Tissue Engineering Applications." *Trends Biomater. Artif. Organs.* 18.2(2005):219-224.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Murdan. "Electro-Responsive Drug Delivery from Hydrogels." *J. Control. Release.* 92(2003):1-17.
Nagai et al. "A Varient of Yellow Fluorescent Protein with Fast and Efficient Maturation for Cell-Biological Applications." *Nat. Biotechnol.* 20.1(2002):87-90.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_004119, Apr. 14, 2013.

(56) References Cited

OTHER PUBLICATIONS

NCBI Accession No. NM_006274.2, Mar. 31, 2013.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Niamlang et al. "Electrically Controlled Release of Salicylic Acid from poly(p-phenylene vinylene) Polyacrylamide Hydrogrls." *Int. J. Pharm.* 371(2009):126-133.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohashi et al. "Surgical Excision Combined with Autologous Whole Tumor Cell Vaccination is an Effective Therapy for Murine Neuroblastoma." *J. Ped. Surg.* 41(2006):1361-1366.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acqusition of Effector Cell Phenotype During Lethal Infection." *Immunity.* 31.5(2009):772-786.
Orner et al. "Arrays for the Cominatorial Exploration of Cell Adhesion." *J. Am. Chem. Soc.* 126.35(2004):10808-10809.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmuity After Reversal of a Functionality Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor α Gene Expression in Respiratory and Peripheral Muscles." *Arch. Bronconeumol.* 38.7(2002):311-316. (Spanish Original and English Abstract).
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lympphoblastic Leukemia (ALL R3): An Open-Label Randomised Trail." *Lancet.* 376(2010):2009-2017.
Partridge et al. "Conversion of mdx Myofibres From Dystrophin-Negative to Positive by Injection of Normal Myoblasts." *Nature.* 337.6203(1989):176-179.
Pedersen et al. "Induction of Regulatory Dendritic Cells by Desamthasone and 1α,25-Dihydroxyvitamin D3." *Immunol. Lett.* 91(2004):63-69.
Pelinkovic et al. "Tissue Engineering and Gene Therapy of the Muscoskeletal System with Muscle Cells." *Z. Orthrop. Ihre Grenzgeb.* 138.5(2000):402-406. (German Original and English Abstract).

Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Intersitital Diffusion of Macromolecules: Crainial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocyctic Cells." *Bioconjugate Chem.* 13.2(2002):216-223.
Pope et al. "Organ-Specific Regulation of the CD8 T Cell Response to *Listeria monocytogenes* infection." *J. Immunol.* 166(2001):3402-3409.
Porter et al. "Separation of Natural Populations of Coliform Bacteria from Freshwater and Sewage by Magnetic-Bead Cell Sorting." *J. Microbiol. Meth.* 33.3(1998):221-226.
Pouzet et al. "Factors Affecting Functional Outcome After Autologous Skeletel Myoblast Transplantation." *Ann. Thorac. Surg.* 71(2001):844-851.
Pulendran et al. "Fit3-Ligand and Granulocyte Colony-Stimulating Factor Mobilize Distinct Human Dendritic Cell Subsets In Vivo." *J. Immunol.* 165(2000):566-572.
Qu et al "Developmental of Approaches to Improve Cell Survival in Myoblast Transfer Therapy." *J. Cell. Biol.* 142.5(1998):1257-1267.
Qu-Peterson et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Qui et al. "Environment-Sensitive Hydrogels for Drug Delivery." *Adv. Drug Deliv. Rev.* 53.3(2001):321-339.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rappolee et al. "Syndecan-Regulated Receptor Signaling." *J. Cell. Biol.* 149.5(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles and mdx and Control Mice." *Eur. J. Neurosci.* 10(1998):366. (Abstract #153.07).
Reis e Sousa. "Activation of Dendritic Cells: Translating Innate into Adaptive Immunity." *Curr. Opin. Immunol.* 16.1(3005):21-25.
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co--glycolide) Particle Size on Gas-Formed Scaffolds." *J. Biomater. Sci. Polym. Ed.* 15.12(2004):1561-1570.
Ridway et al. "Inhibition of Dll4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rizzo et al. "An Improved Cyan Fluorescent Protein Variant Useful for FRET." *Nat. Biotechnol.* 22.4(2004):445-449.
Rosenberg et al. "Cancer Immunotherapy: Moving Beyond Current Vaccines." *Nat. Med.* 10.9(2004):909-915.

(56) References Cited

OTHER PUBLICATIONS

Roth et al. "SC68896, a Novel Small Molecule Proteasome Inhibitor, Exerts Antigiloma Activity In vitro and In vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.
Rowley et al. "Alginate Type and RGD Density Control Myoblast Pheotype." *J. Biomed. Mater. Res.* 60.2(2002):217-233.
Rowley et al. "Biomaterials to Spatially Regulate Cell Fate." *Adc. Mater.* 14.12(2002):886-889.
Rowley et al. "Alginate Hydogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Factilitates Signaling." *J. Biol. Chem.* 276.3(2001):32977-32983.
Ryten et al. "ATP Regulates the Differentiation of Mammalian Skeletal Muscle by Activation of a P2Xh Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Salem et al. "Defining the Antigen-Specific T-Cell Reponse to Vaccination and Poly(I:C)/TLR3 Signaling." *J. Immunother.* 28.3(2005):220-228.
Salvador et al. "Combination of Immune Stimulating Adjuvants With Poly(lactide-co-glycolide) Microspheres Enhances the Immune Response of Vaccines." *Vaccine.* 30.3(2011):589-596.
Salvay et al. "Inductive Tissue Engineering with Protein and DNA-Releasing Scaffolds." *Mol. Biosyst.* 2.1(2006):36-48.
Sano et al. "Swift Development of Protective Effector Functions in Naive CD8+ T Cells Against Malana Liver Stages." *J. Exp. Med.* 194.2(2001):173-179.
Sansonetti. "The innate Signaling of Dangers and the Dangers of Innate Signaling." *Nat. Immunol.* 7.12(2006):1237-1242.
Sarkar et al. "Condensation of Oligonucleotides Assembled into Nicked and Gapped Duplexes: Potential Structures of Oligonucleotides Delivery." *Nucleic Acids Res.* 33.1(2005):143-151.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response to Uterine Epithelial Cells to TLR3 Agonist Poly(I:C). *J. Immunol.* 174(2005):992-1002.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell.* 102.6(2000):777-786.
Shakweh et al. "Design and Characerization of Poly(lactide-co-glycolide) Small Particulate Systems for the Delivery of Immunostimulant CpG Oligonucleotide." *J. Nanosci. Nanotechnol.* 6.9-10(2006):2811-2820.
Shaner et al. "Improved Monomeric Red, Orange and Yellow Fluorescent Proteins Derived from *Discoma* sp. Red Fluorescent Protein." *Nat. Biotechnol.* 22.12(2004):1567-1572.
Shansky et al. "Letter to the Editor: A Simplified Method for Tissue Engineering Skeletel Muscle Oranoids In Vitro." *In Vitro Cell. Dev. Biol.* 33(1997):659-661.
Sheehan et al. "Skeletal Muscle Satellite Cell Proliferation in Reponse to Members of the Fibroblast Growth Factor Family and Hapatocyte Growth Factor." *J. Cell. Physiol.* 181.3(1999):499-506.
Sheridan et al. "Bioabsorbable Polymer Scaffolds for Tissue Engineering to Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4514-4524.
Shoichet et al. "Stability of Hydrogels Used in Cell Encapsulation: An In Vitro Comparison of Alginate and Afarose." *Biotechnol. Bioeng.* 50(1996):374-381.
Shortman et al. "Steady-State and Inflammatory Dendritic-Cell Development." *Nat. Rev. Immunol.* 7(2007):19-30.
Sick et al. "WNT and DKK Determine Hair Folicle Spacing Through a Reaction-Diffusion Mechanism." *Science.* 315.5804(2006):1447-1450.
Silva et al. "Material-Based Depolyment Enhances Efficacy of Endothelial Progenitor Cells." *PNAS.* 105.38(2008):14347-14352.
Silva et al. "Spatiotemporal Control of Vascular Endothelial Growth Factor Delivery From Injectable Hydrogels Enhaces Angiogenesis." *J. Thromb. Haemot.* 5.3(2007):590-598.
Skokos et al. "CD8-DCs Induce IL-12-Independent Th1 Differentiation Through Delta 4 Notch-Like Liganf in Reponse to Bacterial LPS" *J. Exp. Med.* 204.7(2007):1525-1531.
Skuk et al. "Efficacy of Myoblast Transplantation in Nonhuman Primates Following Simple Intramuscular Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immbolization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug. Deliv.* 5.5(2008):543-566.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.
Sun et al. "Sustained Vascular Endothelial Growth Factor Delivery Enhances Angiogensis and Perfusion in Ischemic Hind Limb." *Pharm. Res.* 22.7(2005):1110-1116.
Takahashi et al. "Induction of Pluripotent Stem Cells from Adult Human Fibroblasts by Defined Factors." *Cell.* 131.5(2007):861-872.
Takeshita et al. "Therapeutic Angiogenesis." *J. Clin Invest.* 93.2(1994):662-670.
Tamura et al. "Immunotherapy of Tumors with Autologous Tumor-Derived Heat Shock Protein Preparations." *Science.* 278.3(1997):117-120.
Tanaka et al. "Collapse of Gels in an Electric Field." *Science.* 218(1982):467-469.
Tatsumi et al. "HGF/SF Is Present in Normal Adult Skeletal Muscle and is Capable of Activating Satellite Cells." *Dev. Biol.* 194.1(1998):114-128.
ten Dijke et al. "Growth Factors for Wound Healing." *Nat. Biotechnol.* 7(1989):793-798.
Thurston et al. "The Delta Paradox: DLL4 Blockade Leads to More Tumor Vessels but Less Tumour Growth." *Nat. Rev. Cancer.* 7.5(2007):327-331.
Tidball. "Inflammatory Cell Reponse to Acute Muscle Injury." *Med. Sci. Sports. Exerc.* 27.7(1995):1022-1032.
Tomer et al. "Electrically Controlled Release of Macromolecules from Cross-Linked Hyalauronic Acid Hydrogels." *J. Control. Release.* 33.3(1995):405-413.
Tourniaire et al. "Polymer Microarrays for Cellular Adhesion." *Chem. Commun.* 20(2006):2118-2120.
Tsien. "The Green Fluorescent Protein." *Annu. Rev. Biochem.* 67(1998):509-544.

(56) References Cited

OTHER PUBLICATIONS

Turing. "Discussion: Turing's Theory of Morphogenesis—It's Infulence on Modelling Biological Pattern and Form." *Bull. Math. Biol.* 52.1-2(1990):119-159.
Turing. "The Chemical Basis of Morphogenesis." *Philosophical Transactions of the Royal Society of London, Series B.* 237.641(1952):37-72.
Uchida et al. "Immunization by Particle Bombardment of Antigen-Loaded poly-(DL-lactide-co-glycoide) Microspheres in Mice." *Vaccine.* 12(2006):2120-2130.
Urbanek et al. "Stem Cell Niches in the Adult Mouse Heart." *PNAS.* 103.24(2006):9226-9231.
van Duin et al. "Triggering TLR Signaling in Vaccination." *Trends Immunol.* 27.1(2006):49-55.
Vandenburgh et al. "Tissue-Engineered Skeletal Muscle Organoids for Reversible Gene Therapy." *Hum. Gene Ther.* 17(1996):2195-2200.
Vieira et al. "The Bulk of Endogenously Produced IgG2a is Elminated From the Serum of Adult C57BL/6 Mice With a Half-Life of 6-8 Days." *Eur. J. Immunol.* 16.7(1986):871-874.
Viera et al. "The Half-Lives of Serum Immunoglobins in Adult Mice." *Eur. J. Immunol.* 18.2(1988):313-316.
Villadangos et al. "Instrinsic and Cooperative Antigen-Presenting Functions of Dendritic-Cell Subsets in vivo." *Nat. Rev. Immunol.* 7.7(2007):543-555.
Valladangos. "Presentation of Antigens by MHC Class II Molecules: Getting the Most Out of Them." *Molec. Immunol.* 38.5(2001):329-346.
von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and ☐-Cell Savage." *Endocrinol. Metab. Clin. North Am.* 38.2(2009):303-317.
Wan et al. "Peritonal Macrophage Uptake, Pharmacokinetics and Biodistribution of Macrophage-Targeted PEG-fMLF (*N*-Formyl-Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.
Wang et al. "Evolution of New Nonantibody Proteins via Iterative Somatic Hypermutation." *PNAS.* 101.48(2004):16745-16749.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Werning et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wright et al. "Muscle-Based Gene Therapy and Tissue Engineering for the Musculoskeletal System." *Drug Disc. Today.* 6.14(2001):728-733.
Xie et al. "Preparation and Application of Surface-Coated Superparamagnetic Nanobeads in the Isolation of Genomic DNA." *J. Magn. Magnetic Mater.* 277.1(2004):16-23.
Yancopoulos et al. "Vascular-Specific Growth Factors and Blood Vessel Formation." *Nature.* 407.6801(2000):242-248.
Yu et al. "Induced Pluripotent Stem Cell Lines Derived from Human Somatic Cells." *Science.* 318.5858(2007):1917-1920.
Yuen et al. "Mimicking Natrure by Codelivery of Stimulant and Inhibitor to Create Temporally Stable and Spatially Restricted Angiogenic Zones." *PNAS.* 107.42(2010):17933-17938.
Yuk et al. "Electric Current-Sensitive Drug Delivery System Using Sodium Alginate/Polyacrylic Acid Composites." *Pharm. Res.* 9.7(1992):955-957.
Zammit et al. "Kinetics of Myoblast Proliferation Show That Resident Satellite Cells are Competent to Fullt Regenerate Skeletal Muscle Fibers," *Exp. Cell Res.* 281.1(2002):39-49.
Zammit et al. "Muscle Satellite Cells Adpot Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zhang et al. "A Comparative Study of the Antigen-Specific Immune Response Induced by Co-Delivery of CpG OGN and Antigen Using Fusion Molecules of Biodegradable Microparticles." *J. Pharma. Sci.* 98.12(2007):3283-3292.
Zhao et al. "Active Scaffolds for On-Demand Drug and Cell Delivery." *PNAS.* 108.1(2011):67-72.
Zhao et al. "Directed Cell Migration via Chemoattractant Released from Degradable Microspheres." *Biomat.* 26(2005):5048-5063.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.
Suh, SW, et al., Effect of different particles on cell proliferation in polymer scaffolds using a solvent-casting and particulate leaching technique, ASIAO J, 48(5):460-4; Sep.-Oct. 2002.

* cited by examiner

10,647,959 B2

CELL-FRIENDLY INVERSE OPAL HYDROGELS FOR CELL ENCAPSULATION, DRUG AND PROTEIN DELIVERY, AND FUNCTIONAL NANOPARTICLE ENCAPSULATION

RELATED APPLICATIONS

This application is a national stage application, filed under 35 U.S.C. § 371, of International Application No. PCT/US2012/033208, filed Apr. 12, 2012, which claims the benefit of priority under 35 U.S.C. § 119(e) to U.S. Provisional Application No. 61/479,774, filed Apr. 27, 2011, the contents of which are incorporated herein by reference in their entireties.

FIELD OF THE INVENTION

The invention relates to polymer scaffolds for cell-based tissue engineering.

BACKGROUND

Tissue engineering is an approach for regeneration, replacement, and improvement of the functions of damaged tissues by manipulating materials according to the specific structure or function of the desired tissues. Porous and biodegradable polymer scaffolds, e.g., three dimensionally interconnected scaffolds, are utilized as a structural supporting matrix or as a cell adhesive substrate for cell-based tissue engineering. A highly open porous structure with interconnected pores is required to achieve sufficient cell seeding and migration within the scaffold, as well as to facilitate mass transfer of nutrients, oxygen, and metabolite waste for sequential proliferation and differentiation of large quantity of cells. Current approaches to generate porous networks in polymer scaffolds include gas foaming, salt leaching, and freeze drying; however, the limitations of those processes include irregular pore sizes, shapes, and structures, as well as limited interconnectivity. As such, there is a pressing need in the art to develop improved structured polymer scaffolds with interconnected pores.

SUMMARY OF THE INVENTION

The invention described herein provides the fabrication of cell-friendly inverse opal hydrogels that also allow cell-encapsulation in the hydrogel matrix. An inverse opal hydrogel scaffold device comprising a polymer matrix and a sacrificial porogen in which the porogen comprises an ionically-crosslinked polymer, a thermosensitive polymer, a thermoresponsive polymer, a pH-sensitive polymer, or a photocleavable polymer. The polymer matrix is made of a durable polymer relative to the sacrificial porogen such that the polymer matrix withstands physical or chemical changes that cause porogen sacrifice. For example, polymer matrix is covalently crosslinked, withstands a change (e.g., increase) in temperature, withstands a pH change (e.g., decrease) or change in ionic strength or composition (e.g., contact with a divalent cation chelator), or withstands exposure to light (e.g., UV light).

For tissue engineering and cell scaffold applications, the polymer matrix further comprises an isolated cell, e.g., a eukaryotic cell. By "isolated cell" is meant a cell that has been separated from the other cells, components, and/or environment that naturally accompany it. Alternatively, the matrix contains prokaryotic cells such as bacteria. For example, the polymer matrix is crosslinked and comprises an isolated cell encapsulated in the crosslinked polymer matrix. An exemplary polymer matrix comprises a synthetic polymer such as one that is covalently crosslinked. Examples of polymer matrices include poly(lactide-coglycolide) (PLGA; a copoly lactic acid/glycolic acid polymer), poly(acrylic acid), polyethylene glycol (PEG), poly (vinyl alcohol), or polyphosphazene.

The sacrificial porogen comprises an ionically-crosslinked polymer, a thermosensitive polymer, a thermoresponsive polymer, a pH-responsive polymer, or a photo-cleavable polymer. Exemplary polymers for a porogen include alginate, collagen, gelatin, fibrin, agarose, hyaluronic acid, or chitosan as well as thermosensitive polymer such as agarose, gelatin, or collagen, poly(N-isopropylacrylamide), poly(N-ethylacrylamide), poly(N-cyclopropymethacrylamide), poly(N-methyl-N-ethylacrylamide), poly(N-acryloylpyrrolidine), poly(N-ethylmethacrylamide), poly(N-cyclopropylacrylamide), poly(N-cyclopropylacrylamide), poly (N,N-diethylacrylamide), poly(N-isopropylacrylamide), poly(N-vinylcaprolactam), poly(N-n-propylmethacrylamide), poly(N-methyl-N-isopropylacrylamide), poly(N-n-propylacrylamide), poly(N-methyl-N-n-propylacrylamide), and poly(N-acryloylpiperidine).

Hydrogel (also called aquagel) is a network of polymer chains that are hydrophilic, and are sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content. Hydrogel shaped as an inverted opal exhibits much higher swelling ratios, and its swelling kinetics is an order of magnitude faster as well. The engineered scaffolds (i.e., inverse opal hydrogels) described herein possess desirable mechanical and optical properties that can facilitate tissue regeneration while allowing for continuous high-resolution optical monitoring of cell proliferation and cell-cell interaction within the scaffold.

Methods of producing an inverse opal hydrogel with open, interconnected pores are carried out by compressing a plurality of template porogen particles into a mold, and subsequently adding a composition comprising a polymer solution and a plurality of cells to the interstitial space between template porogen particles in the mold to polymerize the template porogen particles. The template porogen particles are removed from the mold, thereby producing an inverse opal hydrogel with open, interconnected pores, wherein the cells are encapsulated in the inverse opal hydrogel. The template porogen particles are removed without using toxic organic solvents or lyophilization. For example, thermosensitive hydrogel beads are removed by controlling the temperature to change the solid phase of the beads. The template porogen particle is an ionically crosslinked polymer, a thermosensitive polymer, a thermoresponsive polymer, a pH-responsive polymer, or a photo-cleavable polymer.

For example, the ionically crosslinked polymer is alginate. The ionically crosslinked polymer is removed by adding a metal-chelating agent selected from the group consisting of citric acid, ethylenediamine, ethylenediaminetetraacetic acid (EDTA), diethylenetriaminepentaacetic acid (DTPA), and N,N-bis(carboxymethyl)glycine (NTA).

Suitable thermosensitive polymers include agarose, gelatin, and collagen. The thermosensitive polymer is removed by increasing the temperature of the polymer, thereby altering the phase of the polymer to liquid phase. Examples of photocleavable polymers include chromophore-based cross-linkers for photodegradable hydrogels, (4-vinylpyridine) (P4VP) and poly (methylmethacrylate).

Thermoresponsive polymers include poly(N-isopropylacrylamide), poly(N-ethylacrylamide), poly(N-cyclopropymethacrylamide), poly(N-methyl-N-ethylacrylamide), poly(N-acryloylpyrrolidine), poly(N-ethylmethacrylamide), poly(N-cyclopropylacrylamide), poly(N-cyclopropylacrylamide), poly(N,N-diethylacrylamide), poly(N-isopropylacrylamide), poly(N-vinylcaprolactam), poly(N-n-propylmethacrylamide), poly(N-methyl-N-isopropylacrylamide), poly(N-n-propylacrylamide), poly(N-methyl-N-n-propylacrylamide), and poly(N-acryloylpiperidine). Thermoresponsive polymers are removed by increasing the temperature above a lower critical solution temperature (LCST) to reduce the size of the template particles.

The hydrogels described herein have open, interconnected pores of various diameters, e.g., 1 μm pores, 10 μm pores, 50 μm pores, 100 μm pores, 250 μm pores, 500 μm pores, 750 μm pores, 1,000 μm pores, 1,500 μm pores, 2,000 μm pores, 2,500 μm pores, or 3,000 μm pores. Exemplary hydrogels have pores that are 600 μm, 1000 μm, or 1,500 μm in diameter.

Cell-adhering peptides such as Arg-Gly-Asp (RGD) are optionally used to modify the hydrogels described herein. In some cases, the hydrogels described herein comprise a first and a second plurality of cells. For example, the first plurality of cells is comprised within the hydrogel matrix, and the second plurality of cells is added to the open, interconnected pores. The first plurality of cells and the second plurality of cells are selected from the group consisting of mesenchymal stem cells, stromal cells, cancer cells, dendritic cells, macrophages, neutrophils, natural killer cells, or fibroblast cells. Preferably, the first plurality of cells and the second plurality of cells are different cell types.

Methods of producing an inverse opal hydrogel with open, interconnected pores are carried out by compressing a plurality of template porogen particles into a mold, adding a composition comprising a polymer solution and an agent to the interstitial space between template porogen particles in the mold to polymerize the template porogen particles, and removing the template porogen particles, thereby producing an inverse opal hydrogel with open, interconnected pores. The agent is selected from the group consisting of a drug, a nanoparticle (e.g., magnetic nanoparticles or gold nanoparticles), a growth factor (e.g., vascular endothelial growth factor (VEGF), platelet derived growth factor (PDGF), brain derived neurotrophic factor (BDNF), epidermal growth factor (EGF), or fibroblast growth factor (FGF)), a cytokine (e.g., interferon gamma (IFN-γ), erythropoietin (EPO), thrombopoietin (TPO), interleukin-1 (IL-1), IL-4), a chemokine (e.g., a CC chemokine, a CXC chemokine, a C chemokine, or a CX3C chemokine), a hormone (e.g., insulin, growth hormone, vasopressin, testosterone, or cortisol), a protein, a nucleic acid, or a small molecule. In one example, nanoparticles are encapsulated within the hydrogel matrix, and cells are dispersed within the open-interconnected pores.

Compositions comprising an inverse opal hydrogel with open, interconnected pores are produced by the methods described above.

For example, provided is a composition comprising an inverse opal hydrogel with open, interconnected pores comprising a first plurality of cells encapsulated in a hydrogel matrix and a second plurality of cells in the open, interconnected pores, wherein the first plurality of cells encapsulated in the hydrogel matrix occupy an interstitial space between the open, interconnected pores. The first plurality of cells and the second plurality of cells are selected from the group consisting of mesenchymal stem cells, stromal cells, cancer cells, dendritic cells, macrophages, neutrophils, natural killer cells, or fibroblast cells. For example, the hydrogel comprises gelatin or poly(ethylene glycol) (PEG).

By "substantially pure" is meant a nucleic acid, polypeptide, or other molecule that has been separated from the components that naturally accompany it. Typically, the polynucleotide, polypeptide, or other molecule is substantially pure when it is at least 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DETAILED DESCRIPTION

Figure 1:
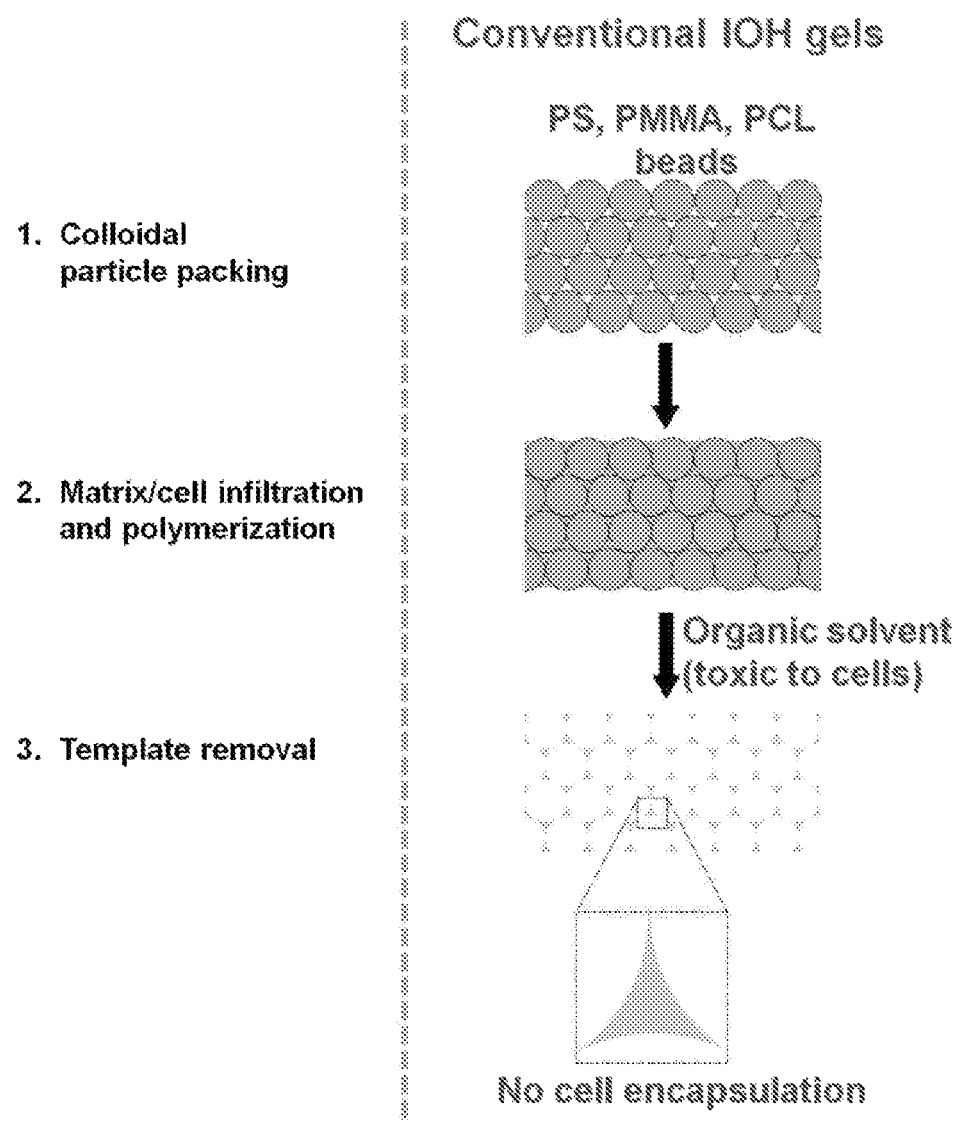
FIG. 1 is a schematic of the utilization of conventional inverse opal hydrogels (IOHs) prior to the invention described herein.

The hydrogel compositions described herein provide a mechanically robust, defined micro-environment for ex vivo cell loading and/or in vivo cell infiltration, as well as adhesion and motility cues to support cell migration and interactions. The cell-compatible or cell-friendly polymer structures, macroporous "inverse opal" hydrogels, comprises interconnected arrays of pores to accommodate the size of a eukaryotic cell. "Opal" refers to the crystalline array of close-packed spheres and "inverse" denotes that this array contains negative space, or pores.

The invention provides the fabrication of inverse opal hydrogels, e.g., composed of gelatin or poly(ethylene glycol) (PEG), that allow not only seeding of cells on porous hydrogels, but also encapsulation of cells in a hydrogel matrix. The elasticity of inverse opal hydrogels was controlled and the hydrogels were modified with the cell-adhering peptide, Arg-Gly-Asp (RGD). The use of the inverse opal hydrogel as 3D scaffolds was evaluated in a culture of mesenchymal stem cells encapsulated in matrix and seeded on pores of the hydrogel. Furthermore, the hydrogel systems described herein are used for the examination of tumor-stromal interactions.

Tissue engineering is a promising approach for regeneration, replacement, or improvement of the functions of damaged tissues by manipulating materials according to the specific structure or function of the desired tissues (R. Langer, Adv Mater 2009, 21, 3235). Porous and biodegradable polymer scaffolds, especially three-dimensionally interconnected scaffolds, has been examined for use as a structural supporting matrix or as a cell adhesive substrate for cell based tissue engineering (S. J. Hollister, Adv Mater 2009, 21, 3330). A highly open porous structure with well interconnected pores is required to achieve sufficient cell seeding and migration within the scaffold as well as to facilitate mass transfer of nutrients, oxygen, and metabolite waste for sequential proliferation and differentiation of large quantity of cells. Various approaches have been proposed to generate porous networks in polymer scaffolds, including gas foaming (D. J. Mooney et al., Biomaterials 1996, 17, 1417; L. D. Harris, et al., J Biomed Mater Res 1998, 42, 396; Y. S. Nam, et al., Journal of Biomedical Materials Research 2000, 53, 1), salt leaching (M. H. Sheridan, et al., J Control Release 2000, 64, 91; L. Lu, et al., Biomaterials 2000, 21, 1837; C. J. Liao, et al., Journal of Biomedical Materials Research 2002, 59, 676), and freeze drying (P. X. Ma, R. Zhang, J Biomed Mater Res 1999, 46, 60; K. Whang, et al., Biomaterials 2000, 21, 2545; A. J. Thornton, et al., Transplantation 2004, 77, 1798). However, prior to the invention described herein, the substantial limitations of current methods include irregular pore sizes, shapes, and structures, as well as limited connectivity. Prior to the invention described herein, inverse opal structured polymer scaffolds were proposed to provide uniform pore size and 3-dimensional pore interconnectivity for cell culture (N. A. Kotov, Y. F. Liu, S. P. Wang, C. Cumming, M. Eghtedari, G. Vargas, M. Motamedi, J. Nichols, J. Cortiella, Langmuir 2004, 20, 7887; Y. F. Liu, S. P. Wang, J. W. Lee, N. A. Kotov, Chemistry of Materials 2005, 17, 4918; Y. J. Zhang, S. P. Wang, M. Eghtedari, M. Motamedi, N. A. Kotov, Advanced Functional Materials 2005, 15, 725; A. N. Stachowiak, D. J. Irvine, Journal of Biomedical Materials Research Part A 2008, 85A, 815; S. W. Choi, J. W. Xie, Y. N. Xia, Advanced Materials 2009, 21, 2997).

Prior to the invention described herein, solid beads, such as polystyrene (PS), poly (methyl metalcrylate) (PMMA) or poly(caprolactone) (PCL) were used as sacrificial templates, while silicate, polyacrylamide (PAM), chitosan, poly(ethylene glycol) (PEG), or poly(lactic-co-glycolic acid) (PLGA) were used as the polymer matrix (FIG. 1). However, in the conventional inverse opal hydrogel systems described previously, it was necessary to use toxic organic solvents or acidic solutions to remove the template beads and/or to use a freeze drying process, which preclude the possibility of cell encapsulation in the inverse opal polymer matrix (FIG. 1). The resulting conventional hydrogels were only used for cell-seeding on the surface of pores after fabrication.

Prior to the invention described herein, cells could not be encapsulated in porous scaffolds prepared by other conventional fabrication methods due to the use of organic solvents, freeze drying of scaffolds, or high pressure of gas (D. J. Mooney, D. F. Baldwin, N. P. Suh, J. P. Vacanti, R. Langer, Biomaterials 1996, 17, 1417; L. D. Harris, B. S. Kim, D. J. Mooney, J Biomed Mater Res 1998, 42, 396; Y. S. Nam, J. J. Yoon, T. G. Park, Journal of Biomedical Materials Research 2000, 53, 1; M. H. Sheridan, L. D. Shea, M. C. Peters, D. J. Mooney, J Control Release 2000, 64, 91; L. Lu, S. J. Peter, M. D. Lyman, H. L. Lai, S. M. Leite, J. A. Tamada, S. Uyama, J. P. Vacanti, R. Langer, A. G. Mikos, Biomaterials 2000, 21, 1837; C. J. Liao, C. F. Chen, J. H. Chen, S. F. Chiang, Y. J. Lin, K. Y. Chang, Journal of Biomedical Materials Research 2002, 59, 676; P. X. Ma, R. Zhang, J Biomed Mater Res 1999, 46, 60; K. Whang, T. K. Goldstick, K. E. Healy, Biomaterials 2000, 21, 2545; A. J. Thornton, E. Alsberg, M. Albertelli, D. J. Mooney, Transplantation 2004, 77, 1798).

Taken together, prior to the invention described herein, porous polymer scaffolds were used as supports for subsequent cell seeding and growth in pores. As described herein, the encapsulation of cells in the matrix of scaffolds and the seeding of other cells in the pores allows the interior of the matrix and the pores within the matrix to provide extracellular environments to the cells. Furthermore, manipulating different cells in controllable environments in hydrogels allows for the examination of cancer cell-stromal cell interactions and paracrine effects on stem cell proliferation and differentiation. The methods described herein provide new material systems for ex vivo cell production and manipulation.

Figure 2:
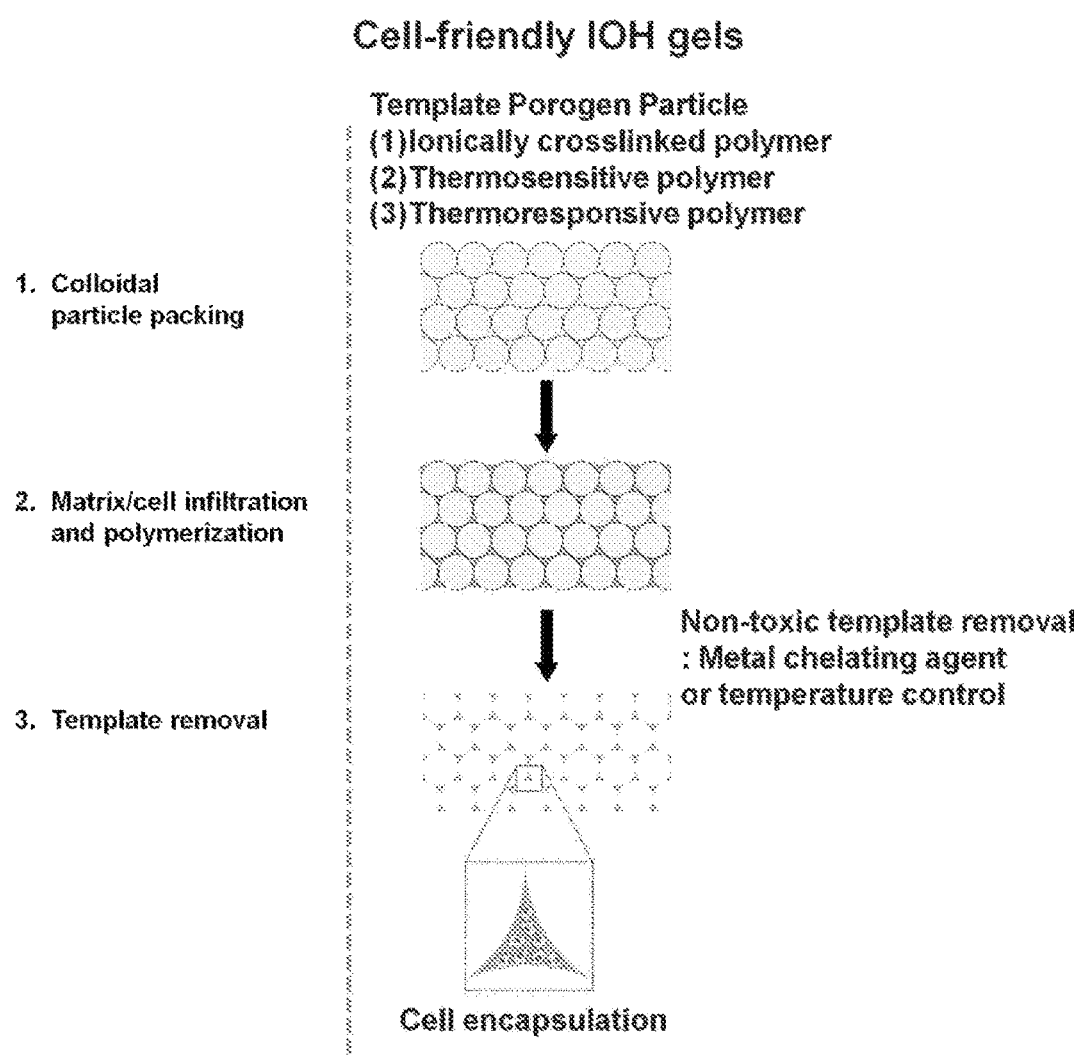
FIG. 2 is a schematic showing "cell-friendly" IOHs produced by the methods described herein.

The invention described herein provides the fabrication of cell-friendly inverse opal hydrogels that also allow cell-encapsulation in the hydrogel matrix (FIG. 2). As described herein, this is achieved by using sacrificial templates (usually polymers) that are removed through cell-friendly routes without using toxic organic solvents. The cell-friendly routes of removing the sacrificial polymer template are determined by the type of polymer template. Suitable sacrificial templates include ionically crosslinked polymers (e.g., alginate), thermosensitive polymers (e.g., agarose, gelatin, collagen) and thermoresponsive polymers (e.g., poly (N-isopropylacrylamide), poly(N-ethylacrylamide), poly(N-cyclopropymethacrylamide), poly(N-methyl-N-ethylacrylamide), poly(N-acryloylpyrrolidine), poly(N-ethylmethacrylamide), poly(N-cyclopropylacrylamide), poly(N-cyclopropylacrylamide), poly(N,N-diethylacrylamide), poly(N-isopropylacrylamide), poly(N-vinylcaprolactam), poly(N-n-propylmethacrylamide), poly(N-methyl-N-isopropylacrylamide), poly(N-n-propylacrylamide), poly(N-methyl-N-n-propylacrylamide), poly(N-acryloylpiperidine)).

Ionically crosslinked hydrogel beads (e.g., alginate) are removed by using various metal-chelating agents including citric acid, ethylenediamine, ethylenediaminetetraacetic acid (EDTA), diethylenetriaminepentaacetic acid (DTPA), N,N-bis(carboxymethyl)glycine (NTA), etc. The chelating agents bind with metal ions used as the crosslinker of templating beads, which results in the generation of pores via the dissociation of metal ions and polymers forming beads. Thermo-sensitive hydrogel beads (e.g., agarose, gelatin, collagen) are removed by increasing the temperature to change the solid phase of polymer beads to liquid phase. Thermo-responsive polymer beads (e.g., poly(N-isopropylacrylamide), poly(N-ethylacrylamide), poly(N-cyclopropymethacrylamide), poly(N-methyl-N-ethylacrylamide), poly (N-acryloylpyrrolidine), poly(N-ethylmethacrylamide), poly(N-cyclopropylacrylamide), poly(N-cyclopropylacrylamide), poly(N,N-diethylacrylamide), poly(N-isopropylacrylamide), poly(N-vinylcaprolactam), poly(N-n-propylmethacrylamide), poly(N-methyl-N-isopropylacrylamide), poly(N-n-propylacrylamide), poly(N-methyl-N-n-propylacrylamide), poly(N-acryloylpiperidine)) are removed by controlling the temperature above lower critical solution temperature (LCST) to reduce the size of template beads, and the resulting smaller beads readily escape from the outer polymer matrix to generate pores. Other stimuli-responsive polymers (e.g., pH-responsive polymer, photo-cleavable polymer, etc.) are also suitable in similar routes.

A variety of materials including natural polymers (e.g., collagen, gelatin, alginate, fibrin, agarose, hyaluronic acid, chitosan, etc.) and synthetic polymers (e.g., PEG, PLGA, poly(acrylic acid), poly(vinyl alcohol), polyphosphazene, etc.) are used for making the polymer matrix between template beads.

To prepare the inverse opal hydrogel encapsulated with cells, the template polymer beads are close-packed in molds of varying shapes/sizes, and the polymer solution mixed with cells is infiltrated into the interstitial space of template beads (FIG. 2). After polymerization of polymer matrix via photopolymerization, redox polymerization, or other polymerization to form crosslinked matrix encapsulating cells, template beads are dissolved and removed to generate pores through appropriate routes mentioned above. This removal of template beads occurs in aqueous solution without using toxic organic solvents or lyophilization, as those processes prohibit cell encapsulation in conventional inverse opal hydrogel systems. The prepared inverse opal hydrogels are rinsed with buffer solution to wash out the residual polymers of templates, and cultured in cell culturing condition (37° C., 5% $CO_2$) to maintain the viability of cells encapsulated in the inverse opal hydrogel matrix.

The structures of inverse opal hydrogels are controllable by using different sizes and different geometry of template polymers. For example, spherical pores are generated from polymer bead template. Polymer templates with an elongated shape are prepared through electrospinning, which results in elongated pores in the hydrogel after removal of the template particles.

The inverse opal hydrogels described herein are also used as the supporters for different types of cells. The inverse opal hydrogels are separated from cell culture media, and a second type of cell dispersed in appropriate cell culture media are seeded onto the hydrogels by adding the cells into the inverse opal hydrogels dropwise. The second type of cells attach on the surface of the inverse opal hydrogel without any additional cell culture media. After the cells have attached to the hydrogel, the excess unattached cells around the inverse opal hydrogel are removed. Finally, the inverse opal hydrogels encapsulating one cell type and seeded with another cell type are cultured for further study.

The system described above is utilized to examine the paracrine effect between cells and the cell-cell interaction between different cells. Suitable combinations of cells include cancer cell-dendritic cell, cancer cell-mesenchymal stem cells, cancer cell-fibroblast, dendritic cell-mesenchymal stem cell, and other various cells.

Prior to the invention described herein, previous 3-dimensional cell culture systems using matrigel or other 3 dimensional biomaterials usually used the same matrix without any physical separation between cells, i.e., the cells were co-encapsulated in the same matrix or co-seeded on the same surface of matrix or culture dish. The inverse opal hydrogels described herein make it possible to culture different cell types in different physical space, thereby mimicking the natural cellular microenvironment. By physically separating cells, the paracrine effect (e.g., the effect of soluble factors from one type of cells on another type of cells) is examined. For example, the paracrine effect of cancer cells and stromal cells (fibroblast, immune cells, stem cells, etc.) is examined. The inverse opal hydrogel system described herein is also utilized to study previous culture systems.

In addition to cell encapsulation, the methods described herein are used for general encapsulation and delivery of drugs, proteins, or growth factors, etc. Prior to the invention described herein, when the organic solvent was used to generate pores in the conventional inverse opal systems, the encapsulated molecules of drugs, proteins, or growth factors lost their function due to exposure to the organic solvent. Also, the remaining organic solvent would have a toxic effect when placed in a living organism. As described herein, the mild conditions for pore removal in the current invention circumvents the problems derived from using organic solvents.

For example, various chemical drugs including small molecules and functional proteins (growth factors, cytokines, chemokines, hormones, etc) are mixed with the polymer precursor solution to be added into the template beads in the mold. After polymerization of the polymer precursors and removal of the template beads, the encapsulated molecules are released slowly. The release profiles depend on crosslinking density, the affinity of molecules to the polymer chain, the size of molecules, etc. In this context, the inverse opal hydrogels are used as delivery systems for the cells encapsulated in the hydrogel or the cells outside the hydrogel.

The methods described herein also encapsulate functional nanoparticles to actuate the porous hydrogel systems to release cells, drugs, proteins, and growth factors on demand. The nanoparticles are encapsulated in the hydrogel in a similar manner in which cells and drugs are encapsulated. Specifically, the functional nanoparticles are mixed with polymer precursors and added into the template beads in the mold. For example, magnetic nanoparticles or gold nanoparticles are encapsulated in the polymer matrix and the resulting porous hydrogels are responsive to an external magnetic field or light, respectively. The guest molecules are released upon detection of the external stimulus. In the case of magnetic nanoparticles, the external magnetic force modulates the volume of pores in the inverse opal hydrogel due to its high porosity. The guest molecules encapsulated or seeded in the inverse opal hydrogels are released by the mechanical forces via convection. In addition, both magnetic nanoparticles and gold nanoparticles are used as hyperthermic moieties. Magnetic nanoparticles and gold nanoparticles generate heat by alternating magnetic fields and irradiation with lasers, respectively. Thus, both magnetic and gold nanoparticles allow thermal motion of the polymer matrix and the encapsulated guest molecules, which accelerates the release rate of guest molecules.

Example 1: Alginate Beads as a Sacrificial Template

Figure 3:
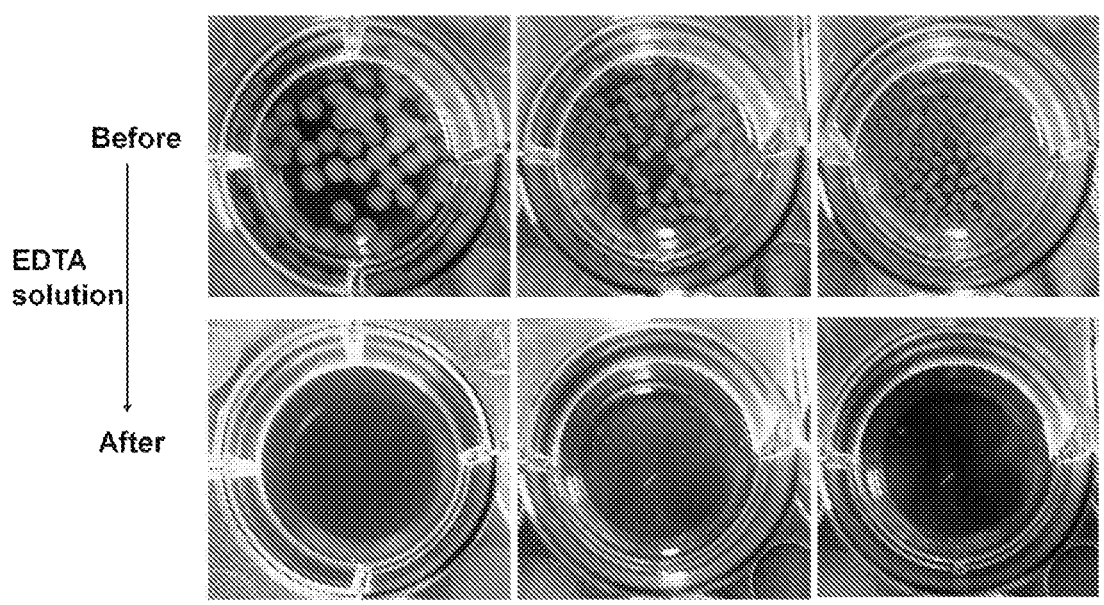
FIG. 3 is a series of photomicrographs demonstrating that ethylenediaminetetraacetic acid (EDTA) efficiently dissolves alginate beads in IOHs.

Described herein is an example of the fabrication of a cell-friendly inverse opal hydrogel. Alginate beads, formed using Ca2+-crosslinking were used as the porogen, and 50 mM EDTA solution, a metal chelating agent, was used as the template removal solution. To evaluate if EDTA can dissolve the alginate beads efficiently, three different sized alginate beads were prepared using 2% alginate solution in 100 mM Ca2+ solution (FIG. 3, upper row). Rhodamine-labeled bovine serum albumin (BSA) was encapsulated in alginate beads to visualize the beads and their dissolution. The resulting alginate beads were incubated in 50 mM EDTA solution under shaking. After 20 min, all alginate beads dissolved in EDTA solution and lost their spherical morphology, and this resulted in a pink solution due to released rhodamine-labeled BSA from alginate beads (FIG. 3, lower row). This demonstrates that the alginate beads were used as sacrificial template by using EDTA as leaching solution.

Example 2: Fabrication of Inverse Opal Hydrogels

Figure 4:
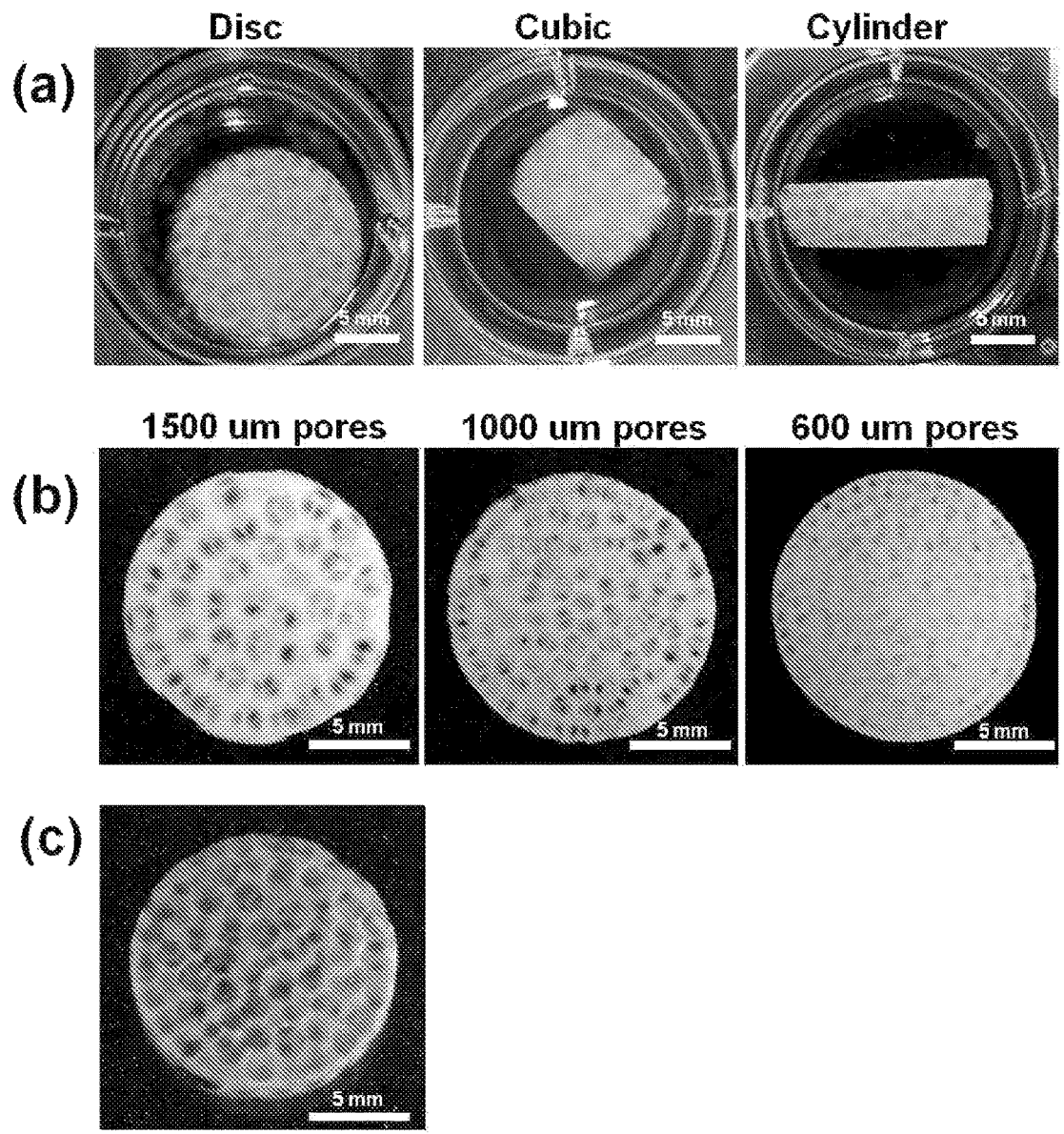
FIG. 4a is a series of photomicrographs showing alginate/gelatin composites with different shapes.
FIG. 4b is a series of photomicrographs showing disc-shaped porous IOHs with different pore sizes.
FIG. 4c is a photomicrograph showing poly(ethylene glycol) (PEG) IOHs.

Inverse opal hydrogels were fabricated using alginate beads as the template and methacrylated-gelatin as the hydrogel precursor (FIG. 4). Alginate beads were close-packed in molds with different shapes. Methacrylated-gelatin (10 wt %) solution was infiltrated by adding to the top of the packed alginate beads, and was subsequently polymerized under UV (365 nm) irradiation for 20 min. FIG. 4a shows alginate/gelatin composites with different shapes, such as disc, cubic, and cylinder. The interstitial space was filled with opaque gelatin hydrogels. Finally, the resulting alginate beads/hydrogel composites were incubated in 50 mM EDTA solution for 1 h at 37° C. under shaking to remove alginate beads. FIG. 4b shows disc-shaped porous IOHs with different pore sizes: 1500, 1000, and 600 um, respectively. The IOH maintained the original structure after removal of templates. The pore size was uniform and 3-dimensionally interconnected pores were clearly observed in each inverse opal hydrogel. The pore size was easily controlled by using different size of alginate beads as templates. As described herein, synthetic polymers are also used for inverse opal hydrogel system. PEG inverse opal hydrogels were prepared using the same protocol (FIG. 4c).

Example 3: EDTA is Non-Toxic to Cells Encapsulated in IOHs

Figure 5:
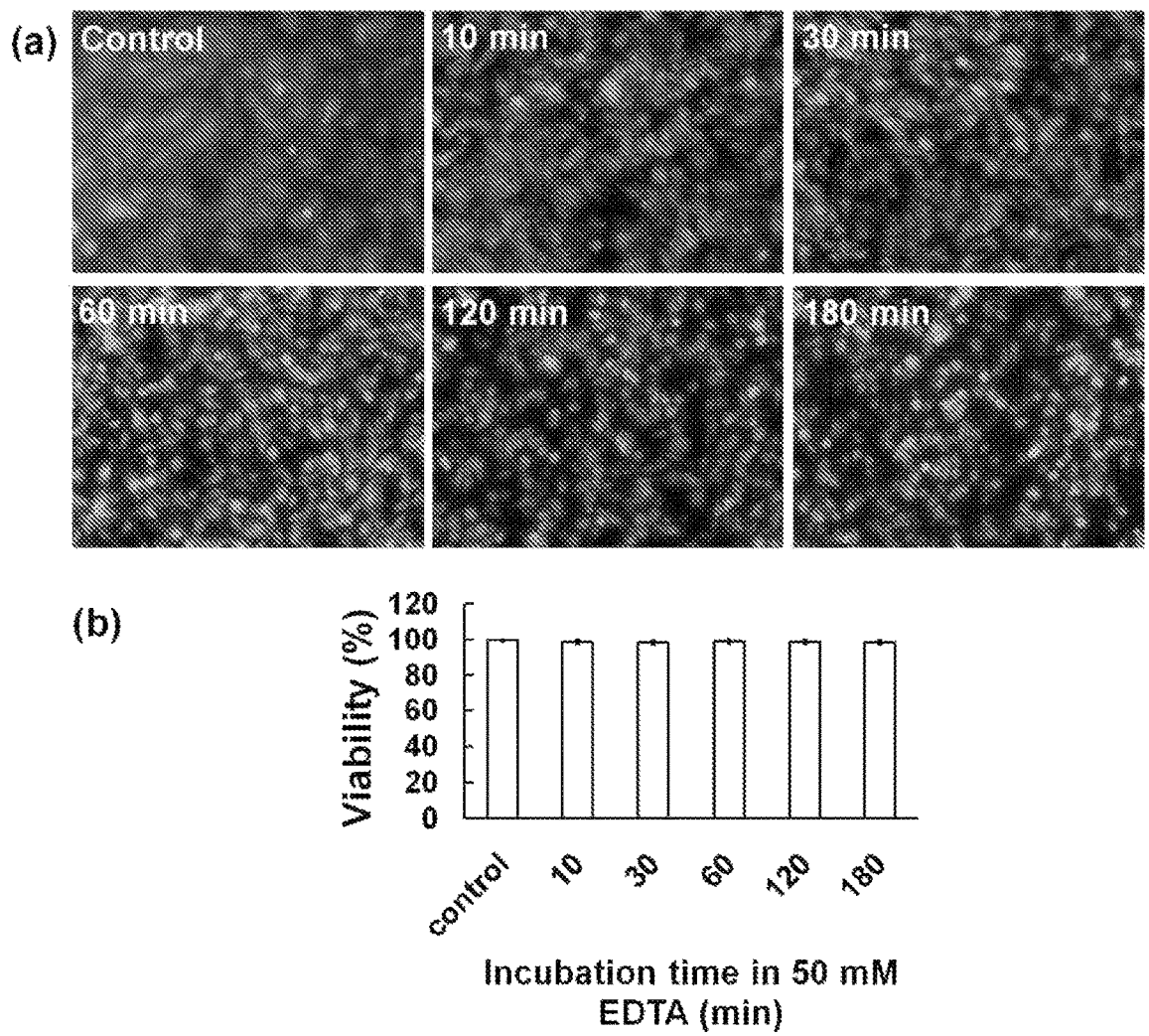
FIG. 5a is a series of photomicrographs showing cell viability after treatment with EDTA for up to 3 hours.
FIG. 5b is a bar chart showing about 98% viability of cells after 3 hour incubation in EDTA.

To evaluate if incubation in EDTA solution is toxic to cells, cell viability was checked after incubation in 50 mM EDTA solution. Mouse mesenchymal stem cells (MSCs) were cultured in a flask, and incubated in a 50 mM EDTA solution for 10, 30, 60, 120, or 180 min. Subsequently, the viability of cells was measured with a live/dead cell assay by using calcein AM and ethidium homodimer-1. Although the cell morphology changed to a round shape, the representative fluorescent images of the live/dead assay showed that there was no significant toxicity of the EDTA solution to the cells for up to 3 h incubation (FIG. 5a). Quantitative analysis also showed ~98% viability even after 3 h incubation in EDTA solution (FIG. 5b). Based on these observations, incubation of the gels in 50 mM EDTA solution for up to 3 h to remove alginate beads was determined as a nontoxic process to cells encapsulated in IOHs.

Example 4: Proliferation of Cells in a Hydrogel Matrix

Figure 6:
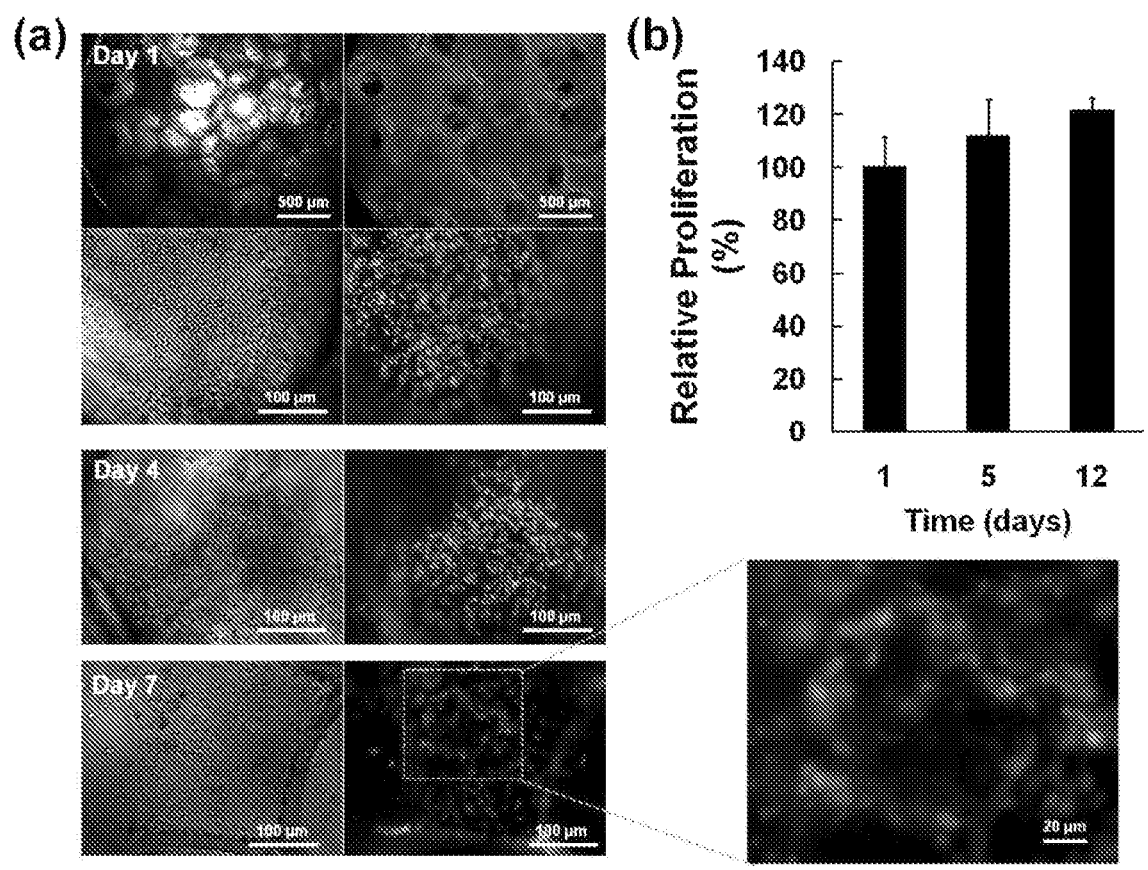
FIG. 6a is a series of photomicrographs showing cell viability after treatment with EDTA for up to 7 days.
FIG. 6b is a bar chart demonstrating the proliferation of cells encapsulated in IOHs.

The encapsulation of cells in IOHs was investigated. Mouse MSCs were dispersed in gelatin-MA at a concentration of $5 \times 10^6$ cells/ml, and added to packed alginate beads in a mold. The gelatin was polymerized under 365 nm UV lamp for 20 min, and the alginate beads were subsequently removed in EDTA solution. The cells were observed on a fluorescent microscope using a fluorescent live/dead assay (FIG. 6a). The cells were alive (stained green) after removal of template alginate beads and were uniformly distributed over the entire scaffolds and the IOHs maintained 3-dimensionlly interconnected pore structures. The morphology of cells changed over time. The cells showed a spherical morphology at day 1, started to spread at day 4, and most of cells were spread in the hydrogel matrix at day 7. The proliferation of cells encapsulated in IOHs (FIG. 6b) was demonstrated using an alamar blue assay in which the fluorescence of the dye increases proportionally to the live cell number. There is an increase of cell number, which means the cells are proliferating in the hydrogel matrix.

Example 5: Proliferation of Cells on the Surface of IOHs

Figure 7:
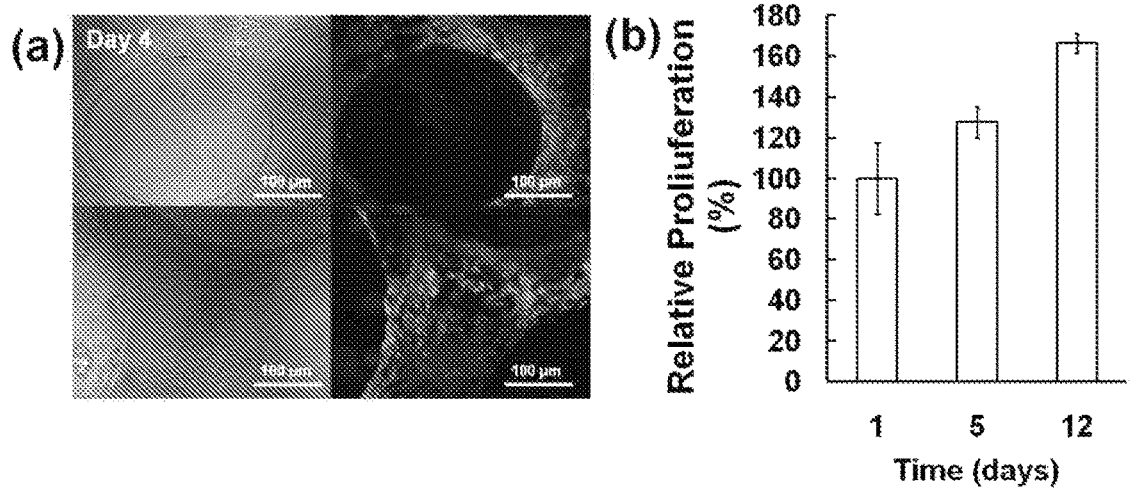
FIG. 7a is a series of photomicrographs demonstrating that the density of cells on the surface of IOHs increased 4 days post seeding.
FIG. 7b is a bar chart showing that cell number in cell-seeded IOHs increased over time.

Cell seeding on the surface of IOHs after the template was removed was also investigated. Gelatin IOH was prepared and mouse MSCs were seeded on IOHs. After 4 days culture, the cells were well-attached on the inner pore surfaces, and the density of cells increased (FIG. 7a). The cell number in cell-seeded IOHs (FIG. 7b) increased over time, which indicates that the cells proliferated on the gel.

Example 6: Proliferation of Cells on the Surface of PEG IOHs

Figure 8:
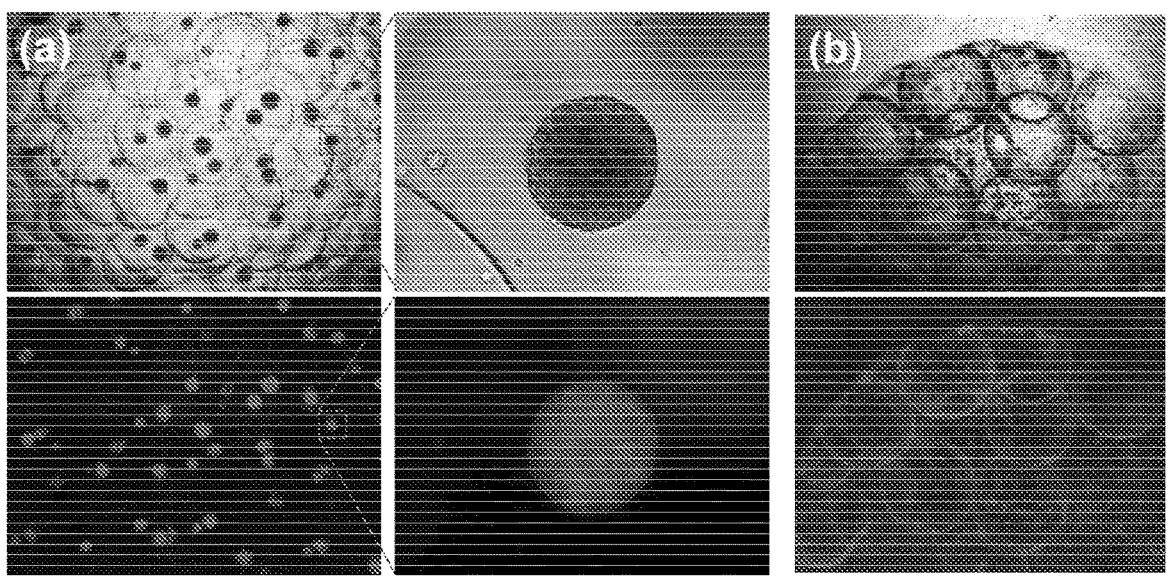
FIG. 8 is a series of photomicrographs showing the proliferation of cells on the surface of PEG without (FIG. 8a) or with (FIG. 8b) Arg-Gly-Asp (RGD) modification.

PEG without (FIG. 8a) and with (FIG. 8b) RGD modification were prepared, and mouse mesenchymal cells (FIG. 8a) or breast cancer cells (FIG. 8b) were seeded on IOHs. As cells cannot attach to the intact PEG hydrogel, the cells formed spherical aggregates in intact PEG IOHs (FIG. 8a). However, the cells were well-attached on the inner pore surfaces of RGD-modified IOH (FIG. 8b) (upper: bright filed images, lower: fluorescent images). Thus, the attachment of seeded cells was controlled by changing the surface functionality.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An inverse opal hydrogel scaffold device comprising a polymer matrix, a plurality of cells encapsulated in the polymer matrix, and a sacrificial porogen,
    wherein said sacrificial porogen is a porogen polymer selected from the group consisting of an ionically-crosslinked polymer, a thermosensitive polymer, a thermoresponsive polymer, a pH-sensitive polymer, and a photocleavable polymer, and
    wherein said sacrificial porogen is removable from said scaffold device by contact with a chelating agent, a change in temperature or pH, or exposure to light to form open, interconnected pores; and
    wherein said polymer matrix occupies an interstitial space between said sacrificial porogen.

2. The inverse opal hydrogel scaffold device of claim 1, wherein said plurality of cells encapsulated in said polymer matrix comprises an isolated eukaryotic cell.

3. The inverse opal hydrogel scaffold device of claim 2, wherein said polymer matrix is crosslinked.

4. The inverse opal hydrogel scaffold device of claim 2, wherein said isolated eukaryotic cell is a mesenchymal stem cell.

5. The inverse opal hydrogel scaffold device of claim 1, wherein said polymer matrix comprises a synthetic polymer.

6. The inverse opal hydrogel scaffold device of claim 1, wherein said polymer matrix comprises covalent crosslinking.

7. The inverse opal hydrogel scaffold device of claim 1, wherein said polymer matrix is selected from the group consisting of a poly(lactide-coglycolide) (PLGA), poly (acrylic acid), polyethylene glycol (PEG), and poly (vinyl alcohol).

8. The inverse opal hydrogel scaffold device of claim 1, wherein said sacrificial porogen is selected from the group consisting of alginate, collagen, and agarose.

9. The inverse opal hydrogel scaffold device of claim 1, wherein said ionically crosslinked polymer is alginate.

10. The inverse opal hydrogel scaffold device of claim 1, wherein said ionically crosslinked polymer is removable by adding a metal-chelating agent selected from the group consisting of citric acid, ethylenediamine, ethylenediaminetetraacetic acid (EDTA), diethylenetriaminepentaacetic acid (DTPA), and N,N-bis(carboxymethyl)glycine (NTA).

11. The inverse opal hydrogel scaffold device of claim 1, wherein said thermoresponsive polymer is poly(N-isopropylacrylamide).

12. The inverse opal hydrogel scaffold device of claim 1, wherein said hydrogel is modified with a cell-adhering peptide, wherein said cell-adhering peptide is Arg-Gly-Asp (RGD).

13. The inverse opal hydrogel scaffold device of claim 1, wherein said polymer matrix is crosslinked and wherein the scaffold device further comprises an agent encapsulated in said crosslinked polymer matrix.

14. The inverse opal hydrogel scaffold device of claim 13, wherein said agent is selected from the group consisting of a drug, a nanoparticle, a growth factor, and a protein.

15. The inverse opal hydrogel scaffold device of claim 14, wherein said nanoparticle is a magnetic nanoparticle or a gold nanoparticle.

16. An inverse opal hydrogel scaffold device comprising a polymer matrix, a plurality of cells encapsulated in the polymer matrix, and a sacrificial porogen,
    wherein said sacrificial porogen is a porogen polymer selected from the group consisting of an ionically-crosslinked polymer, a thermosensitive polymer, a thermoresponsive polymer, a pH-sensitive polymer, and a photocleavable polymer,
    wherein the hydrogel has open, interconnected pores after removal of the sacrificial porogen by contact with a chelating agent, a change in temperature or pH, or exposure to light,
    wherein said polymer matrix comprises covalent crosslinking, and
    wherein said polymer matrix further comprises an isolated eukaryotic cell encapsulated in said crosslinked polymer matrix which occupies an interstitial space between said sacrificial porogen.

17. The inverse opal hydrogel scaffold device of claim 16, wherein said polymer matrix comprises a synthetic polymer.

18. The inverse opal hydrogel scaffold device of claim 16, wherein said polymer matrix is selected from the group consisting of a poly(lactide-coglycolide) (PLGA), poly (acrylic acid), polyethylene glycol (PEG), and poly (vinyl alcohol).

19. The inverse opal hydrogel scaffold device of claim 16, wherein said sacrificial porogen is selected from the group consisting of alginate, collagen, and agarose.

20. The inverse opal hydrogel scaffold device of claim 16, wherein said ionically crosslinked polymer is alginate.

21. The inverse opal hydrogel scaffold device of claim 16, wherein said thermosensitive polymer is selected from the group consisting of agarose, gelatin, and collagen.

22. The inverse opal hydrogel scaffold device of claim 16, wherein said thermoresponsive polymer is poly(N-isopropylacrylamide).

23. The inverse opal hydrogel scaffold device of claim 16, wherein said isolated eukaryotic cell is a mesenchymal stem cell.

24. The inverse opal hydrogel scaffold device of claim 16, wherein the scaffold device further comprises an agent encapsulated in said polymer matrix and wherein said agent is selected from the group consisting of a drug, a growth factor, and a protein.

\* \* \* \* \*